(12) United States Patent
Tzachev

(10) Patent No.: US 12,409,146 B2
(45) Date of Patent: *Sep. 9, 2025

(54) SOLID LIPID NANOPARTICLE FOR INTRACELLULAR RELEASE OF ACTIVE SUBSTANCES AND METHOD FOR PRODUCTION THE SAME

(71) Applicant: LEAD BIOTHERAPEUTICS LTD, Sofia (BG)

(72) Inventor: Christo Tzachev Tzachev, Sofia (BG)

( * ) Notice: Subject to any disclaimer, the term of this patent is extended or adjusted under 35 U.S.C. 154(b) by 77 days.

This patent is subject to a terminal disclaimer.

(21) Appl. No.: 18/156,432

(22) Filed: Jan. 19, 2023

(65) Prior Publication Data
US 2023/0165804 A1   Jun. 1, 2023

Related U.S. Application Data

(62) Division of application No. 16/772,204, filed as application No. PCT/IB2017/001582 on Dec. 12, 2017, now abandoned.

(51) Int. Cl.
| A61K 9/51 | (2006.01) |
| A61K 31/045 | (2006.01) |
| A61K 31/4545 | (2006.01) |
| A61K 31/58 | (2006.01) |
| A61K 38/46 | (2006.01) |

(52) U.S. Cl.
CPC .......... *A61K 9/5146* (2013.01); *A61K 9/5123* (2013.01); *A61K 9/5176* (2013.01); *A61K 9/5192* (2013.01); *A61K 31/045* (2013.01); *A61K 31/4545* (2013.01); *A61K 31/58* (2013.01); *A61K 38/465* (2013.01)

(58) Field of Classification Search
CPC .. A61K 9/5146; A61K 9/5123; A61K 9/5176; A61K 9/5192; A61K 31/045; A61K 31/4545; A61K 31/58; A61K 38/465
See application file for complete search history.

(56) References Cited

U.S. PATENT DOCUMENTS

| 12,036,329 B2 * | 7/2024 | Tzachev | A61K 9/10 |
| 2014/0079785 A1 * | 3/2014 | Jensen | A61P 17/00 |
| | | | 514/180 |

FOREIGN PATENT DOCUMENTS

CN       103784421 A   *   5/2014

OTHER PUBLICATIONS

Cipolla, David, et al. "Modifying the release properties of liposomes toward personalized medicine." Journal of pharmaceutical sciences 103.6 (2014): 1851-1862. (Year: 2014).*
Kumbhar, Popat S., et al. "D-α-tocopheryl polyethylene glycol succinate: a review of multifarious applications in nanomedicines." OpenNano 6 (2022): 100036. (Year: 2022).*
Mirchandani, Yashika, Vandana B. Patravale, and S. Brijesh. "Solid lipid nanoparticles for hydrophilic drugs." Journal of Controlled Release 335 (2021): 457-464. (Year: 2021).*
D'Souza, Susan. "A review of in vitro drug release test methods for nano-sized dosage forms." Advances in pharmaceutics 2014.1 (2014): 304757. (Year: 2014).*
Kheradmandnia, Soheila et al. "Prepapration and Characterization of ketoprofen-loaded solid lipid nanoparticles made from beeswax and carnauba wax.", Nanomedicine: Nanotechnology, Biology and Medicine, 6.6, pp. 753-759. (Year: 2010).*
Shahidi, Fereidoon, and Adriano Costa De Carnargo. "Tocopherols and tocotrienols in common and emerging dietary sources: Occurence, applications, and health benefits." International Journal of Molecular Sciences, 17.10, 1745. (Year: 2016).*
Garg, Anuj, Kripal Bhalala, and Devendra Singh Tomar. "In-situ single pass intestinal permeability and pharmacokinetic study of developed Lumefantrine loaded solid lipid nanoparticles." International journal of pharmaceutics 516.1-2: 120-130. (Year: 2017).*
Arias, Mauricio A., et al. "Carnauba wax nanoparticles enhance strong systemic and mucosal cellular and humoral immune responses to HIV-gp140 antigen." Vaccine 29.6 (2011): 1258-1269. (Year: 2011).*

* cited by examiner

*Primary Examiner* — Abigail Vanhorn
(74) *Attorney, Agent, or Firm* — PatShegen IP; Moshe Pinchas

(57) ABSTRACT

The invention relates to solid lipid nanoparticle for intracellular release of active substances, can be used in the pharmaceutical industry, in the medicine, cosmetics, as well as for food supplements. Solid lipid nanoparticle has spherical shape with a diameter of 15-100 nm, the lipid is a solid lipid selected from natural plant wax or its synthetic analogue, as the surface acting agent is used TMDSC. The particles of solid lipid nanoparticle is characterized with high melting point, high lipophilicity and low (or lack) of in-vitro dissolution profile. The system is lipase-resistant and is capable to freely penetrate through cell membranes into cells where to release the active substance(s) due to an intracellular digestion with controllable depo-effect. In a second aspect, the invention relates to a method of production of the solid lipid nanoparticle. The preferred technology for production of the compositions is a Phase Inversion Temperature method.

9 Claims, 14 Drawing Sheets

(21a) R (21b) R (21c) R

SOLID LIPID NANOPARTICLE FOR INTRACELLULAR RELEASE OF ACTIVE SUBSTANCES AND METHOD FOR PRODUCTION THE SAME

TECHNICAL FIELD

The invention relates to solid lipid nanoparticle for intracellular release of active substances, can be used in the pharmaceutical industry, in the medicine and cosmetics and for production of food supplements, and to the method for production the same.

BACKGROUND ART OF THE INVENTION

Solid lipid particulate systems such as solid lipid nanoparticles (SLN), lipid microparticles (LM) and lipospheres have been sought as alternative carriers for therapeutic compounds. The lipid nanoparticles were developed as alternative to traditional carriers such as polymeric nanoparticles and liposomes. They are useful for many different administration routes: dermal and mucosal, oral, intravenous/parenteral, pulmonary but also ocular, as well as in cosmetics and for non-pharmaceutical use, e.g. in nutraceuticals. The field of application usually depends on the active ingredients, which are incorporated.

The ability to incorporate drugs into nanocarriers offers a new prototype in drug delivery that could lead to the bioavailability enhancement along with control of the speed of active ingredient release and site-specific drug delivery. The lipid matrix of SLN can protect labile active ingredients from hydrolysis and/or oxidation (Gohla, S. et al. J. Microencapsul. 18:149-158 (2001); Schafer-Korting, M. ef al. Adv. Drug Del. Rev. 59:427-443 (2007).

It is known that SLNs have generally spherical shape with a diameter of 10-1000 nm. The lipid phase (lipid core) of the SLN is in a solid state and it comprises a lipid and an emulsifier system containing at least one emulsifier, which may or may not have a role in the nanoparticles stability. The lipid phase can be any fatty substance (or mixture of such), which is solid at the storage temperature of the SLN. Suitable lipids are for example mono-, di- or triglycerides, fatty acids, steroids, lipid peptides and waxes. As a carrier system the SLN comprises also at least one lipophilic and/or amphiphilic active ingredient.

For the preparation, materials are homogenized under high pressure in a dispersion medium (water, an aqueous solution or a liquid miscible with water) in a melted or softened state, or the inner phase is dispersed under high pressure in a dispersion medium in a solid state, whereby the solid phase is finely broken down. (WO1993005768)

Various technical solutions are known in the prior art for compositions of SLN. Some of them are the subject of patent applications or patents. Differences between the known compositions for solid lipid nanoparticles can be identified in the used lipid compounds, in used surfactants or the micellar solubilisers. Examples of lipid nanoparticulate systems as carriers for delivery of drugs are described in many patents/applications, including, but not limited to: US2017020819, US2016106869, US2016030305, US2016022550, US2015258221, U.S. Pat. No. 9,084,818, WO2006102768, WO2015007398, US2014017329, EP2919756, CN103239423, WO2013105101, CN102258475, CN105560215.

Examples of surface modified lipid nanoparticles are described in patent/patent applications, including, but not limited to US2017000899, US2016106869, CN102793672, US2015086484, U.S. Pat. No. 8,715,736, WO2010126319, WO2009053937, US2008311214, KR100792557, KR100703254. Disadvantage of these known solid lipid nanoparticles is their large size as well as their high lipid content. Because of high content of mono-, di- or triglycerides, the lipid core of these solid lipid particles is object of enzymatic disintegration by lipases and the active substances can't be targeted for release in the cell.

In WO 2006/102768, SLNs have been developed where a solid tocopherol or a solid derivative thereof and triglyceride formed a lipid core of the nanoparticle. The surface of particles was functionalized with hydrophobic electrically charged compound. The obtained particles are melting bellow 55° C., having size above 130 nm.

The SLNs, according to this invention have relatively big particle size, low melting point, and TPGS is used as substance, forming the core of nanoparticles.

U.S. Pat. No. 8,242,165 describes mucoadhesive nanoparticles for a localized or targeted delivery of taxanes and other drugs as analgesics (e.g., morphine and morphine congeners, opioid analgesics, non-opioid analgesics, and the like) to subjects suffering from cancer. The nanoparticles are formed of a hydrophobic core and a hydrophilic surface layer surrounding the hydrophobic core. The hydrophobic core includes the glyceryl mono fatty acid esters, in liquid or in solid state, and the hydrophilic surface layer includes the chitosan. The nanoparticles can include emulsifiers (e.g., polyvinyl alcohol) in amount from about 0.1% to about 5% and/or acids (e.g. citric acid) which may be used in their preparation. The mucoadhesive nanoparticles for a localized or targeted delivery have diameters of less than about 5000 nm and a spherical or elliptical form.

The nanoparticles, according to the invention, have mucoadhesive properties, which are due to chitosan shell of solid lipid nanoparticles. The mucoadhesive compound increases the effect of the therapeutic agent on cancer cells in the sample but this increased therapeutic effect is due to the nanoparticles' interaction with increased (relative to the non-cancer cells) levels of mucin on and/or around the cancer cells. The functionalized shell gives targeting to the liver and mucoadhesive properties allowing the particles to attach to mucus glycoproteins and cell membranes.

There are no known compositions of lipid nanoparticles for an intracell targeting of active substances, which simultaneously to avoid the p-gp efflux mechanism, to be lipase-resistant and to release the incorporated in them active substance only after enzymatic intracellular degradation (digestion) of the nanoparticles.

DISCLOSURE OF INVENTION

The task of the invention is to create a solid lipid nanoparticulate (SLN) carrier, as nontoxic, non-irritating system with controllable depo-effect for transport and delivery of active substances, where the SLN to be with a small size of particles, with low concentration of the lipid phase, with no or significantly lower concentration of the liquid lipid, allowing the lipid to behave as an ordered system with no liquid domains and where the active substance to be encapsulated ("locked") within the hard and insoluble core of the SLN, which particles to have high lipophilicity and extremely low (or lack of) in-vitro dissolution profile, as to indicate simultaneously lipase-resistance and ability to freely penetrate through cell membranes into cells where to release the active substance(s) by an intracellular erosion.

The task of the invention is resolved by creation of a solid lipid nanoparticle for intracellular release of active substances, containing a solid lipid selected from the group of natural plant wax and its synthetic analogues, a surface acting agent d-α-Tocopheryl polyethylene glycol 1000 succinate, an active substance and water. The active substance is incorporated in solid nanoparticle. The components of the solid lipid nanoparticle are in the following quantitative ratios in w/w parts: from 0.01 to 20 parts a natural wax or its synthetic analogues, from 0.01 to 20 parts d-α-Tocopheryl polyethylene glycol 1000 succinate, an active substance from 0.00001 to 10 parts and water in the amount up to 100 w/w parts. The solid lipid nanoparticle has spherical shape with a diameter from 15 to 100 nm.

In a preferred embodiment of the invention, the natural plant wax is carnauba wax.

In certain embodiment, aiming to increase the capacity for inclusion of active substances, the solid lipid nanoparticle, according to the invention, includes in the matrix additionally liquid lipid in an amount up to 20% of the total lipid. The liquid lipid is selected from oils including natural and synthetic oil with high content of Tocotrienol, such as red palm oil, rice bran oil, wheat germ oil, or animal oils.

In one preferred embodiment as liquid lipid can be used mono- or mix of isomers of Tocotrienol. In other certain embodiment the solid lipid nanoparticle, according the invention, includes in the structure of matrix the surface acting agent d-α-Tocopheryl polyethylene glycol 1000 succinate (TPGS) in combination with a polysorbate, selected from polysorbate 20, polysorbate 40, polysorbate 60 or polysorbate 80. The polysorbate is in an amount from 0.01 to 10 w/w parts. In one preferred embodiment the surface acting agent is d-α-Tocopheryl polyethylene glycol 1000 succinate (TPGS) in combination with polysorbate 40.

The active substance incorporated in the SLN matrix according to the invention is selected from drug substances, diagnostic agents, biological products, food supplements, cosmetic products or medical devices.

Solid Lipid Component of Solid Lipid Nanoparticle, According to the Invention

As solid lipid component in the composition, according to the invention, natural and synthetic waxes are useful. However natural wax or its synthetic analog is preferable because of lower crystallinity related with composition complexity. From the natural waxes plant waxes are preferable. From the plant waxes carnauba wax is preferable for the following reasons:

Natural product composed of biocompatible ingredients. It is isolated from the leaves of the palm *Copernicia prunifera*; It is produced and available worldwide in an industrial scale.

The highest melting temperature wax. Carnauba wax contains carboxylic acid residues and other having hydroxyl groups. The hydroxyl groups tie together adjacent carbon chains by hydrogen bonding. These weak cross-links make carnauba wax a hard, relatively high-melting substance, which makes it the hardest of the waxes with very low or lack of solubility in non-polar and polar solvents at room temperature.

Due to its complex composition, it is referred as a crystal matter with amorphous domains. The aliphatic esters contain monocarboxylic acids of average chain length C26 and monohydric alcohols of average chain length C32. The ω-hydroxyesters contained are mixtures of ca. 90% esters of ω-hydroxyacids (C26) and monohydricalcohols (C32) and 10% esters of monocarboxylic acids (C28) and α, ω-diols (C30). Esters containing 4-hydroxy- and 4-methoxycinnamic acids are present mainly as oligomers and polymers. The monomer units of these are diesters of the above-named cinnamic acids with mono- and polyhydric alcohols and ω-hydroxycarboxylic acids. The free alcohols are similar in composition to those in aliphatic esters (Uwe Wolfmeier at all. "Waxes" in Ullmann's Encyclopedia of Industrial Chemistry, Wiley-VCH, Weinheim, 2002).

Adding plasticizers increase the portion of amorphous phase with a maximum reduction of crystallinity at up to 10%. (Zhang Y. at all., B & Achkar, J 2016, "Plasticisation of Carnauba Wax with Generally Recognised as Safe (GRAS) Additives' Polymer, vol 86, pp. 208-219).

Being the hardest among waxes, because of its long chain hydrocarbons composition, and the weak cross linking, carnauba wax is resistant to enzyme degradation in the gastro-intestinal tract and intercellular spaces. That's why it is capable to transport active substances in intact state into the cells.

Carnauba wax particles don't form protein corona with human albumin and other soluble proteins within the human body in contrast with many other lipids.

Surface Acting Agents of Solid Lipid Nanoparticle, According to the Invention

Form the surface acting agents preferable are nonionic surfactants with HLB between 9 and 18. Most preferable they are combinations of nonionic surfactants with resultant HLB value between 9 and 18.

Preferable surface acting agent is d-α-Tocopheryl polyethylene glycol 1000 succinate (TPGS) used alone or more preferable in combination with polysorbates (polysorbate 20, polysorbate 40, polysorbate 60, polysorbate 80). The reason for their combination is that these two surfactants possess additional complementary roles in the composition.

According to the modern understanding, TPGS can inhibit the P-gp activity without affecting the membrane fluidity (Rege, B. D. at all. Effects of nonionic surfactants on membrane transporters in 754 Caco-2 cell monolayers. Eur. J. Pharm. Sci. 16, 237-246, 2002; Yamagata, T. at all., Effect of 867 excipients on breast cancer resistance protein substrate uptake activity. J. Controlled Rel. 124, 1-5, 2007). P-gp ATPase (P-gp energy source of active transport) inhibition caused by TPGS is the main reason for this (Collnot et al., 2007). TPGS was neither a substrate nor a competitive inhibitor in P-gp efflux transport. TPGS does not fluidize the lipid bilayers of cell membranes, and does not inhibit the peptide transporter.

The P-gp ATPase inhibition by surfactants is explained with an allosteric modulation that TPGS binds to the non-transport active binding site (Collnot et al., 2010; Collnot et al., 2007). The commercially available TPGS1000 is so far the most potential efflux pump inhibitor as studied by Lehr et al.

While polysorbates were found to significantly increase the apical-to-basolateral and decrease the basolateral-to-apical (BL-AP) permeability, TPGS exhibits a reduction in the BL-AP permeability in Caco-2 monolayers. Polysorbates inhibit the peptide transporter.

It then can be speculated that according to literature data a combination of TPGS and polysorbate must express synergistic effect on P-gp inhibition. However, reverse effect could also be regarded as possible due to opposite activities on the membrane fluidity: polysorbates fluidize, but tpgs rigidizes the membrane fluidity. That's why the obviousness of the results of combination between TPGS and polysorbate is excluded.

The mechanism of membrane permeability enhancement are indicated in the Table 1

TABLE 1

The mechanism of membrane permeability enhancement

|  | Membrane fluidity | P-gp ATPase inhibition | P-gp transporter |
|---|---|---|---|
| TPGS | − | + | − |
| Polysorbate | + | + | + |

Liquid Lipid Component of Solid Lipid Nanoparticle, According to the Invention

In certain embodiment of the present invention, the composition of solid lipid particle comprises a liquid lipid phase in quantity up to 20% of the total lipid. The liquid lipid is essential to decrease the degree of crystallinity of the carnauba wax structure. Amorphization of the lipid structure increases the loading capacity for active substances. However high levels of liquid lipid will form liquid domains within the particles which can leak out of the particle before it reaches the target or even before its application (during the storage of the formulation). That's why the right portion of the liquid lipid is critical for preservation the "locked" state of the entrapped active ingredient. The liquid lipid in current invention serves to partially weaken the strong crystal structure of carnauba wax in order to increase its capacity for the active substance. Still, the amount of liquid lipid must not exceed the threshold of formation of liquid domains within the lipid particle. This threshold is dynamic and except the liquid lipid amount, it depends on the nature and amount of the rest of ingredients in the particle composition.

The preferred liquid lipid for the present invention is chosen among Tocotrienol mono- or mixed isomers, Red palm oil, annatto oil, rice bran oil, wheat germ oil and other oils and oil concentrates with high content of tocotrienols. Their isoprenoid tails with three unsaturation points allow tocotrienols to increase the inter chain distance preventing the close packing and to produce more flexible aggregates between the dense crystal blocks of the hydrophobic sections of aliphatic esters and hydrocarbons of the carnauba wax.

The invention strategy is to construct of the above described platform for intracellular drug delivery system built on the combination of four interrelated prerequisites:

I. Non-binding to body proteins, hence non-adhesive, free floating through tissue linings, tissues and cells.

II. Robustness to digestive and tissue enzymes.

III. Cell targeting of active substances classified as substrates of the P-glycoprotein.

IV. Intracellular digestion to nontoxic metabolites.

Taken apart all these four basics have been used in the practice before. Surprisingly their combination shows extremely high therapeutic affectivity with potential for multiple times reduction in the usual doses of the applied active substances.

I. Non-Binding to Body Proteins

It is increasingly being accepted that once entered the body, nanoparticles can be recognized by the responsible immune cells as antigens directly or after covering with protein corona. After administration, some nanoparticles can interact with tissue proteins and other molecules. Particle conjugates can be detected by the immune system, evoking a pro-inflammatory response. The protein corona also influences the interactions of particles with the cell membrane. Adsorption of proteins can modify the surface charge and may impart for altered drug targeting/metabolism. (Bogart L K et al. Nanoparticles for Imaging, Sensing, and Therapeutic Intervention. ACS Nano. 2014; 8(4):3107-3122).

The adsorption of proteins on the surface of nanoparticle is governed by protein-nanoparticle binding affinities as well as protein-protein interactions. The most abundant proteins, albumin and fibrinogen, were found on the surface of many types of nanoparticles. Albumin itself shows affinity to hydrophobic surfaces and polyanions. Also, formation of hard (primary) and soft (secondary) corona is associated with increase in particle diameter hence slowed down ability for diffusion and entering cells. (M. Rahman et al., Protein-Nanoparticle Interactions, Springer Series in Biophysics 15, Springer-Verlag Berlin Heidelberg 2013). All these unwanted protein-nanoparticle interactions surprisingly were not observed with the compositions of the present invention in spite of the fact that protein corona has been well documented to assemble with lipid nanoparticles. Lack of such interaction in the present invention may result from the ordered and dense structure of the selected lipids and related reduced mobility of the expanding carboxylic groups of the incorporated fatty acids.

As the main structural component of the composition of present invention yellow carnauba wax or synthetic equivalent contains long-chain fatty acids up to 6%. The carboxylic groups of the fatty acids are oriented towards the particle surface. Such an exposure can potentially lead to a covalent bonding of proteins and amine-terminated peptides. However, such a behavior was not observed with the particles of the present invention. The obvious explanations can be related with the unique composition: the steric effect of the free hydrophilic polyethylene chains and the limited mobility of the carboxyl groups due to the substantial hardness (partial crystallinity) of the particles.

II. Robustness to Digestive and Tissue Enzymes.

Solid lipid particles formulated with wax lipids in particular carnauba wax are highly robust against enzymatic degradation by the lipases of gastrointestinal tract. This is described before in literature (I. Greener Donhowe and O. Fennema, Water vapour and oxygen permeability of wax films, *J. Am. OH Chem. Soc.* 70:867 (1993); Mellema M1, Van Benthum W A, Boer B, Von Harras J, Visser A. Wax encapsulation of water-soluble compounds for application in foods. J Microencapsul. 2006; 23(7):729-40; McClements D J. Encapsulation, protection, and release of hydrophilic active components: potential and limitations of colloidal delivery systems. Adv Colloid Interface Sci. 2015 May; 219:27-53)

This can be explained with their dense crystal blocks made up from hydrophobic sections of high aliphatic esters and hydrocarbons.

Using such a structure as a matrix for inclusion of active substances has never been understood to be attractive as delivery system until now.

The expected effect from encapsulation of lipophilic active substances in such a delivery system is their lock within the particle cores with no (or minimal) release in body fluids (gastrointestinal tract, blood, mucus, liquor, synovial, interstitial and other body liquids).

The present invention relates precisely to such a delivery particulate system where escaping the active substance release in the body fluids and targeting the cell digestion is achieved by intracellular but not interstitial, mucosal or digestive system enzyme degradation or by very slow diffusion out of the particle matrix. The latter is more evident in the presence of unsaturated fatty acids (bees wax) or in the complex particles consisting liquid domains.

Wax esters are hydrolyzed by a bile salt-dependent pancreatic carboxyl esterase, releasing long chain alcohols and fatty acids that are absorbed in the gastrointestinal tract. However, some solid waxes as carnauba wax undergo carboxyl esterase degradation in gastrointestinal tract rather slow. The compositions of the present invention inspite of containing carnauba wax don't show any structure change when exposed to pancreatic lipases for 24 hours.

III. Cell Targeting of Active Substances Classified as Substrates of the P-Glycoprotein (P-Gp).

P-gp is one of the first members of the ATP-binding cassette (ABC). The role of P-gp is likely to protect cells from toxic compounds, preventing them to enter the cytosol and extrude them to the exterior (Fortuna A, Alves G, Falcao A. In vitro and in vivo relevance of the P-glycoprotein probe substrates in drug discovery and development: focus on rhodamine 123, digoxin and talinolol. *J Bioequiv Availab.* 2011). P-gp is expressed on the epithelial cells lining the colon, small intestine, pancreatic ductules, bile ductules, kidney proximal tubules, adrenal gland, respiratory ways, placenta. (Kandimalla, K. K. & Donovan, M. D. Pharm Res (2005) 22:1121) It is also located in the endothelial cells of the blood brain barrier (Ma J D, Tsunoda S M, Bertino J S, Jr, Trivedi M, Beale K K, Nafziger A N. Evaluation of in vivo P-glycoprotein phenotyping probes: a need for validation, Clin Pharmacokinet. 2010; 49(4):223-37). The transporter is over expressed on the surface of many neoplastic cells and restricts cell entry of many of the known antineoplastic drugs. P-gp has broad poly-specificity, recognizing hundreds of compounds or drugs as small as 330 up to 4000 Da (Aller S G, Yu J, Ward A, et al. Structure of P-glycoprotein reveals a molecular basis for poly-specific drug binding. Science (New York, NY). 2009; 323(5922):1718-1722) As the substrate binding pocket sits inside the cellular membrane and needs to be accessed by distribution into the lipid bilayer, the lipophilic and amphiphilic nature of the substrates is to be expected. P-gp can eject a wide range of structurally diverse compounds out of the cells, including anticancer agents, immune suppressants, steroid hormones, calcium channel blockers, beta-adrenoreceptor blockers, cardiac glycosides, among others. Less permeable drugs (weak substrates) may also undergo a substantial extrusion. Thus, it contributes greatly in the extrusion of many drugs penetrated from particular sites of administration (e.g. the intestinal lumen and other mucosal tissues). P-gp is also responsible for enhancing the excretion of drugs out of hepatocytes and renal tubules into the adjacent luminal space. Therefore, P-gp can potentially reduce the absorption and oral bioavailability and decrease the retention time of a number of drugs (Sharom F J. The P-glycoprotein multidrug transporter. Essays Biochem. 2011 Sep. 7; 50(1):161-78). Additionally, it has a role in limiting cellular uptake of drugs from blood circulation into the brain while being present in the BBB.

According to Linardi R L and Natalini C C Multi-drug resistance (MDR1) gene and P-glycoprotein influence on pharmacokinetics and pharmacodymanics of therapeutic drugs. The P-gp efflux transporter located within the blood-brain barrier restricts the uptake of drugs and other molecules within the CNS; drug efflux is a common mechanism of resistance in microorganisms, along the same lines as target modification or production of antibiotic inactivating enzymes; P-gp is over expressed on the surface of cancer cells and prevents drug accumulation inside the tumor, extruding it before can reach the intended target (Ciência Rural 36:336-341, 2006).

Internalization of particles, and more specifically lipid particles in cells, have been described before as means to escape cell membrane efflux mechanisms and other reasons for low bioavailability of active agents. Recent publications uncover the specific mechanisms laying behind the cellular uptake of surface modified lipid particles carrying on their surface ligands (Shang et al., Engineered nanoparticles interacting with cells: size matters. Journal of Nanobiotechnology. 2014, 12:5). Eukaryotic cells use several endocytic pathways to internalize a variety of substances and particles: the clathrin-dependent pathway, phagocytosis, macropinocytosis and the caveolin-dependent pathway. The type of endocytosis depends upon cell type: phagocytosis is characteristic of specialized cells including macrophages, monocytes and neutrophiles; macropinocytosis is characteristic of internalization of polyplexes, and less commonly for lipoplexes (Midoux P, Breuzard G, Gomez J P, Pichon C, 2008 Polymer-based gene delivery: a current review on the uptake and intracellular trafficking of polyplexes. Curr Gene Ther 8:335-52). The type of endocytosis also depends upon the particle size: In receptor-mediated endocytosis, small particles (<250 nm) are mainly internalized through the clathrin-mediated pathway, a nonspecific mechanism. This pathway is initiated by the formation of clathrin-coated pits that leads to the development of early and late endosomes, which ultimately fuse with lysosomes (Rejman J, Oberle V, Zuhorn I S, Hoekstra D. Size-dependent internalization of particles via the pathways of clathrin- and caveolae-mediated endocytosis. Biochem J 377: 159-69, 2004). Larger particles (≥500 nm) generally enter the cells through caveolae (Brodsky F M, Chen C Y, Knuehl C, Towler M C, Wakeham D E. Biological basket weaving: formation and function of clathrin-coated vesicles. Annu Rev Cell Dev Biol 17:517-68, 2001)

Suzuki et al. (doi.org/10.1016/j.ijpharm.2017.01.016) demonstrate that solid lipid particles are internalized into cells via endocytosis and show efficient endosomal escape, delivering siRNA into the cytoplasm.

Still, to my knowledge the current invention discloses for the first time a solid lipid particle composition loaded with active substance(s) intended to escape the p-glycoprotein pump and to deliver it (them) into cells after erosion as a general release mechanism.

The phenomenon opposite to endocytosis, named as exocytosis, is the fusion of inner vesicles with the plasma membrane as a means to transporting molecules either to plasma membrane or to extracellular space. The endocytic and exocytic trafficking are highly dynamic and well-regulated and it has been estimated that cells can internalize up to five times their volume and membrane area in one hour. This way particles not being "digested" within the first hosted cell will enter to the next and so on and finally pass through tens, hundreds or thousands of cells delivering gradually active substance. The main advance of such an in-cell delivery is that the active substance has the chance to meet and interact with the target if the target is intracellular. If, however the target is on the cell surface or intercellular space—the chance is that the active substance is pumped out of the cell in a prolonged action scenario.

Therefore, escaping the p-gp efflux mechanism is part of the fundamentals building the carrier platform of the current invention.

IV. Intracell Digestion to Nontoxic Metabolites

Wax lipid ester bonds generally display good chemical stability at physiologic pH but can be hydrolyzed enzymatically by esterase or lipase activity present in tissues and intracellular compartments. The resulting hydrolysis products can undergo further metabolism by β-oxidation, the natural mechanism for the metabolism of free fatty acids (Hargrove A. Very Long Chain Fatty Alcohols and Acids from Dietary Waxes. Exp Bioi Med 229:215-226, 2004). A huge amount of energy is generated in the form of ATP by mitochondrial oxidation of fatty acids through β-oxidation. Thus, the metabolism of wax particles is energy releasing process, in which the end products are in general carbon dioxide and water (with practically no residual ingredients after cell internalization).

It was found that the particles of the present invention undergo namely intracell digestion but not pancreatic lipase metabolism.

In a second aspect, the invention relates to a method of production of the solid lipid nanoparticles, a structure of a matrix for inclusion of active substances, according to the invention. The preferred technology for production of the compositions of the present invention is a Phase Inversion Temperature method. It consists in convertible temperature-related dehydration of ethoxylated surfactants. At higher temperatures the lipophilicity of the surfactant molecules rises to a point of balance called phase inversion temperature. With further increase in temperature the surfactant behaves as lipophilic and changes the type of resulting emulsion i.e. from o/w to w/o. During this conversion namely form o/w to w/o to o/w nanoemulsions are form spontaneously.

This technology is highly reproducible, uses relatively low temperatures (up to 90° C.), and neither don't require high energy approaches like high pressure or sonication, nor uses organic solvents. According to the method of production, the lipid compound/compounds, surface acting agent and active substance of the preparation of solid lipid nanoparticles are heated up to 90° C.+/−2° C. to melt and stirred until homogeneous clear mixture is obtained. The water is heated up to 90° C.+/−2° C. and added dropwise to the mixture obtained under stirring. The obtained dispersion is cooled down gradually under stirring to 20° C.+/−2° C. to give the nanoparticle dispersion.

Advantages of the composition of SLN of the invention are lack of toxicity, lack of irritation, possibilty of control of depo-effect for transport and delivery of active substances, small size of particles, low content of lipid, no or significantly lower concentration of a liquid lipid, the lipid is partially ordered system with no liquid domains, the active substance is encapsulated ("locked") in the hard and insoluble core of SLN, which particles have high lipophility and low (or lack) of in-vitro dissolution profile, they are also are lipase-resistant and have capability to freely penetrate through cell membranes into cells where only are able to release the active substance(s) by an intracellular erosion.

EXAMPLES

Figure 1:
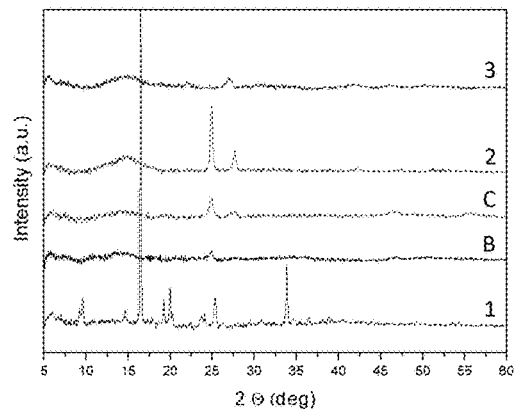
FIG. 1 is a XRD spectra of Menthol (1); carnauba wax (2); TPGS (3); of the composition from example 1B (B) and example 1C (C), which indicate the crystallinity of raw carnauba wax and loaded compositions, changes of its crystallinity but still preserving the ordered state.

Hereinafter, the present invention is described in more detail and specifically with reference to the Examples, which however are not intended to limit the present invention.

Examples 1. Preparation of Lipid Nanoparticles in Variants with and without Active Substances, According to the Invention A. Preparation of Placebo 1% Lipid Nanoparticles For the preparation of placebo 1% lipid nanoparticles are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Water | up to 100 |

For the preparation of lipid nanoparticles are mixed Carnauba wax, Red palm oil concentrate, d-α-Tocopheryl polyethylene glycol 1000 succinate (TPGS) and Polysorbate 40. The mixture is heated up to 90° C.+/−2° C. to melt and stirred until homogeneous clear mixture is obtained. The needed amount of the water is heated up to 90° C.+/−2° C. and it is added dropwise to the homogeneous mixture obtained under stirring.

The obtained dispersion is cooled down under stirring to 20° C.+/−2° C. to give the nanoparticle dispersion.

A'. Preparation of Placebo 1% Lipid Nanoparticles with Pancreatic Lipase 200 UI/g For the preparation of placebo 1% lipid nanoparticles with Pancreatic lipase 200 UI/g are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Pancreatic lipase | 200 UI/g |
| Water | up to 100 |

The lipid nanoparticles are obtained as per the procedure described in Example 1A. The calculated amount of pancreatic lipase is added into the cooled nanoparticle dispersion under steering.

B. Preparation of Placebo 1% Lipid Nanoparticles with 0.1% Oleic Acid

For the preparation of placebo 1% lipid nanoparticles with oleic acid are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Oleic acid | 0.1 |
| Water | up to 100 |

The lipid nanoparticles are obtained as per the procedure described in Example 1A. The calculated amount of oleic acid is added into the cooled nanoparticle dispersion under steering.

C. Preparation of 1% Lipid Nanoparticles with 0.1% Menthol

For the preparation of 1% lipid nanoparticles with Menthol are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Menthol | 0.1 |
| Water | up to 100 |

The lipid nanoparticles are obtained as per the procedure described in Example 1A. The calculated amount of Menthol is added into the cooled nanoparticle dispersion under steering.

D. Preparation of 1% Lipid Nanoparticles with 0.01% Mometasone Furoate (Mometasone Furoate/Lipid=0.83/100)

For the preparation of 1% lipid nanoparticles with Mometasone furoate are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Mometasone furoate | 0.01 |
| Water | up to 100 |

The lipid nanoparticles are obtained as per the procedure described in Example 1. The calculated amount of Mometasone furoate is added into the cooled nanoparticle dispersion under steering.

D'. Preparation of 1% Lipid Nanoparticles with 0.01% Mometasone Furoate and Pancreatic Lipase 200 UI/g For the preparation of 1% lipid nanoparticles with Mometasone furoate and Pancreatic lipase are used the following compounds:

| Compounds | Amount in w/w parts |
|---|---|
| Carnauba wax | 1.00 |
| Red palm oil concentrate (30% tocotrienols) | 0.2 |
| d-α-Tocopheryl polyethylene glycol 1000 succinate (TPGS) | 0.5 |
| Polysorbate 40 | 0.7 |
| Mometasone furoate | 0.01 |
| Pancreatic lipase | 200 UI/g |
| Water | up to 100 |

The lipid nanoparticles are obtained as per the procedure described in Example 1D.

E. Preparation of Lipid Nanoparticles with 0.03% Mometasone Furoate (Mometasone Furoate/Lipid=0.83/100)

For the preparation of lipid nanoparticles with Mometasone furoate are used the following compounds:

| Compounds | Amount in w/w parts |
|---|---|
| Carnauba wax | 3.00 |
| Red palm oil concentrate (30% tocotrienols) | 0.60 |
| d-α-Tocopheryl polyethylene glycol 1000 succinate (TPGS) | 1.50 |
| Polysorbate 40 | 2.7 |
| Mometasone furoate | 0.03 |
| Water | up to 100 |

The lipid nanoparticles are obtained as per the procedure described in Example 1D.

F. Preparation of Lipid Nanoparticles with 0.01% Mometasone Furoate and 0.1% Loratadine For the preparation of lipid nanoparticles with Mometasone furoate and Loratadine are used the following compounds:

| Compounds | Amount in w/w parts |
|---|---|
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.7 |
| Mometasone furoate | 0.01 |
| Loratadin | 0.10 |
| Water | up to 100 |

The lipid nanoparticles are obtained as per the procedure described in Example 1D.

G. Preparation of Lipid Nanoparticles with 0.1% Loratadine (Loratadine/Lipid=8.3%)

For the preparation of a lipid nanoparticles with 0.1% Loratadine are used the following compounds:

| Compounds | Amount in w/w parts |
|---|---|
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.7 |
| Loratadin | 0.10 |
| Water | up to 100 |

The lipid nanoparticles are obtained as per the procedure described in Example 1D.

Test Analyses of the Solid Lipid Nanoparticles, According to the Invention

Analysis of the Particle Size Structure and Morphology

This analysis has been performed by X-ray powder diffraction (XRD). Microstructural studies were performed using XRD with Cu-Kα radiation on a Bruker D8 Advance diffractometer with Cu-Kα radiation in θ-2θ geometry. The tests have been performed of 1 ml samples, which were freeze-dried and desiccated until testing.

Results from XRD analysis of ingredients of the placebo composition 1A are shown in FIG. 1, representing overplayed spectra of: methanol (1), carnauba wax (2); TPGS (3); composition of the solid lipid nanoparticles from example 1B (B); composition of the solid lipid nanoparticles example 1C (C).

Figure 2:
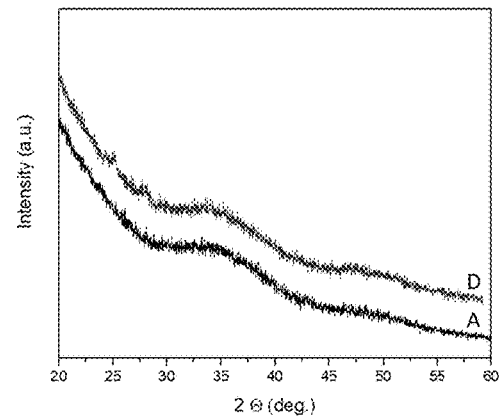
FIG. 2 is a XRD spectra of placebo particles, of the composition from example 1A (A), and the particles, loaded with 0.1% Mometasone—example 1D (D), which indicate decrease of crystallinity of carnauba wax in placebo and loaded compositions.
Figure 3:
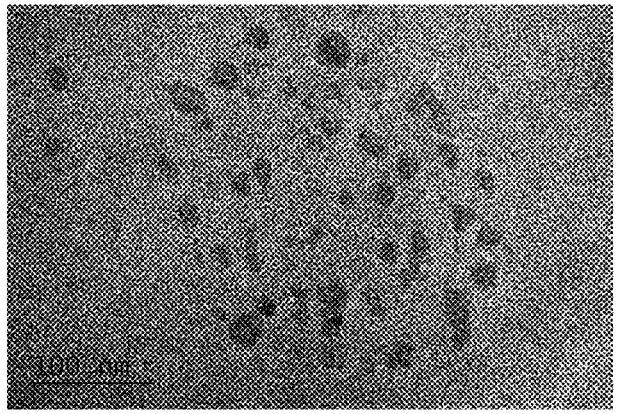
FIG. 3 shows a TEM micrograph of placebo particles, composition from example 1A, which show spherical shape of particles with narrow size distribution in the range between 15 and 35 nm and their position in the space with no tendency to form aggregates.
Figure 4:
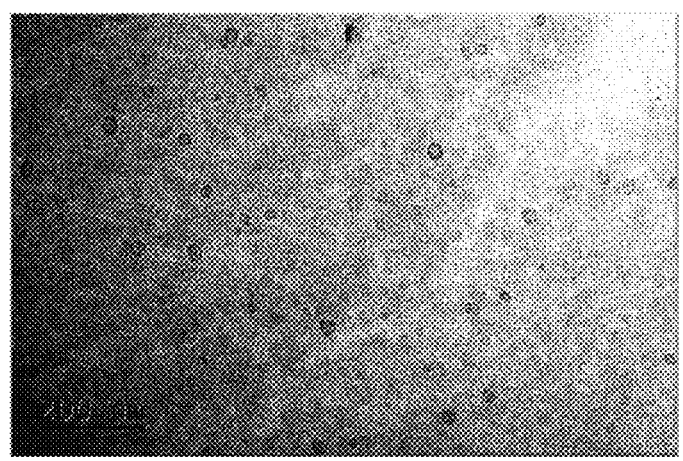
FIG. 4 shows a TEM micrograph of particles, loaded with 0.01% Mometasone furoate—example 1D, which shows spherical shape of particles with narrow size distribution in the range between 15 and 35 nm and their position in the space with no tendency to form aggregates.
Figure 5:
FIG. 5 shows diffraction of particles, loaded with 0.01% Mometasone furoate—example 1D, which corresponds to an amorphous structure. The halo around the bright spot in the center indicates that the electrons are diffracted randomly which is inherent for the amorphous materials. However, a limited degree of crystalline structure was proved in another test with XRD analysis of the SLNs.

Analyses of the particles structure and morphology has been performed also on placebo particles, 1A (A), and particles, loaded with 0.1% Mometasone, example 1D (D) and shown in FIG. 2. Analysis of the obtained XRD spectra indicate that the crystallinity of raw carnauba wax is reduced markedly in placebo and loaded compositions, still preserving the ordered state. The crystallinity corresponding to carnauba component in particles decreases with the decrease in melting temperature of the added active substance (Mometasone furoate, mt 218-220° C.; Menthol, mt 31° C.; oleic acid, mt 13-14° C.).

Tests of Local Structure and Morphology

The tests are performed by:

A. Transmission electron microscopy (TEM). JEOL 2100 transmission electron microscope and a JEOL 2100 XEDS: Oxford Instruments, X-MAX$^N$ 80T CCD Camera ORIUS 1000, 11 Mp, GATAN at accelerating voltage of 200 kV. The analysis was carried out using the Digital Micrograph software.

Selected particle suspensions according to example 1 were diluted 500× and 20 μl were applied on standard holey carbon/Cu grids then left in a desiccator for 72 hours.

The tested samples of placebo (example 1A, FIG. 3) and 0.01% Mometasone furoate loaded particles (example 1D, FIG. 4) show spherical particles with narrow size distribution in the range between 15 and 35 nm. The particles are spread separately with no tendency to form aggregates. The corresponding electron diffraction pattern is shown on FIG. 5. The diffraction pattern corresponds to an amorphous structure. The halo around the bright spot in the center indicates that the electrons are diffracted randomly which is inherent for the amorphous materials. However, a limited degree of crystalline structure was proved with XRD analysis of the SLNs.

B. Atomic Force Microscopy (AFM)

AFM imaging was performed on the NanoScope V system (Bruker Ltd, Germany) operating in tapping mode in air at room temperature.

Selected particle suspensions according to example 1 were diluted 100× and 100 μL were applied on mica support and spin-coated on Precision Spin Coater Model KW-4A (West Chester, PA, USA).

Figure 6:
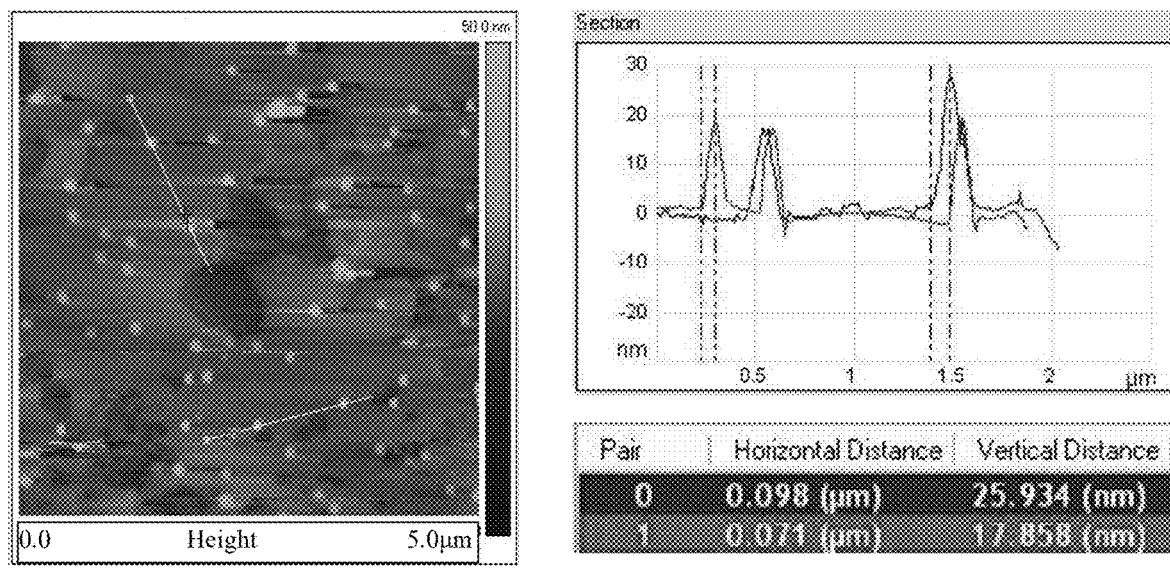
FIG. 6 shows AFM micrograph of placebo particles, according to example 1A, which indicates that particles have spherical shape with narrow size distribution in the range between 15 and 35 nm. The particles are dispersed separately with no tendency to form aggregates.
Figure 7:
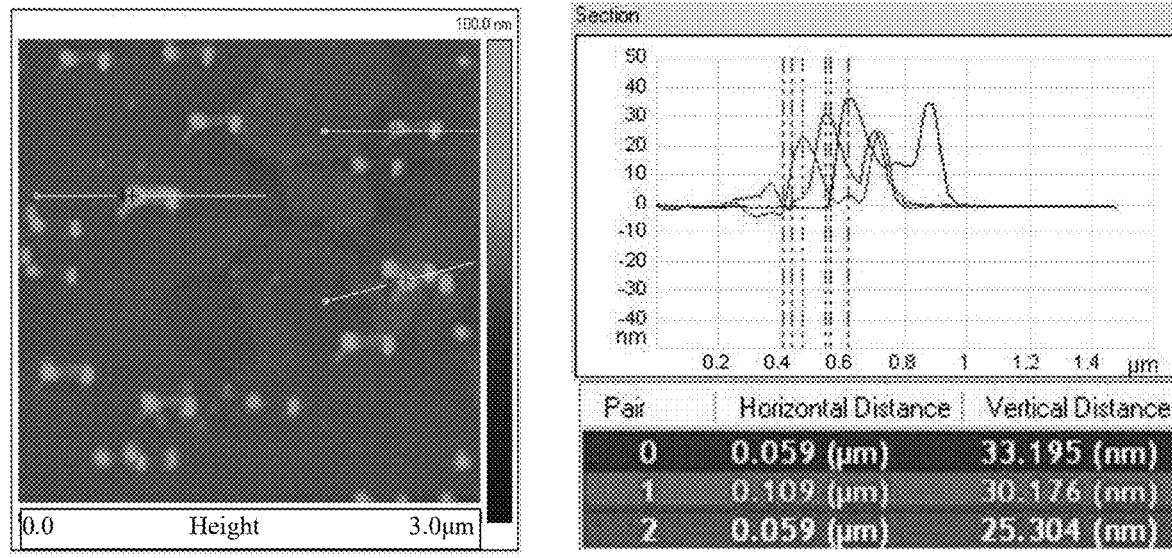
FIG. 7 shows AFM micrograph of particles loaded with 0.03% Mometasone furoate, according to example 1E, which indicates that Mometasone furoate loaded particles have spherical shape with narrow size distribution in the range between 15 and 35 nm. The particles are dispersed separately with no tendency to form aggregates.
Figure 8:
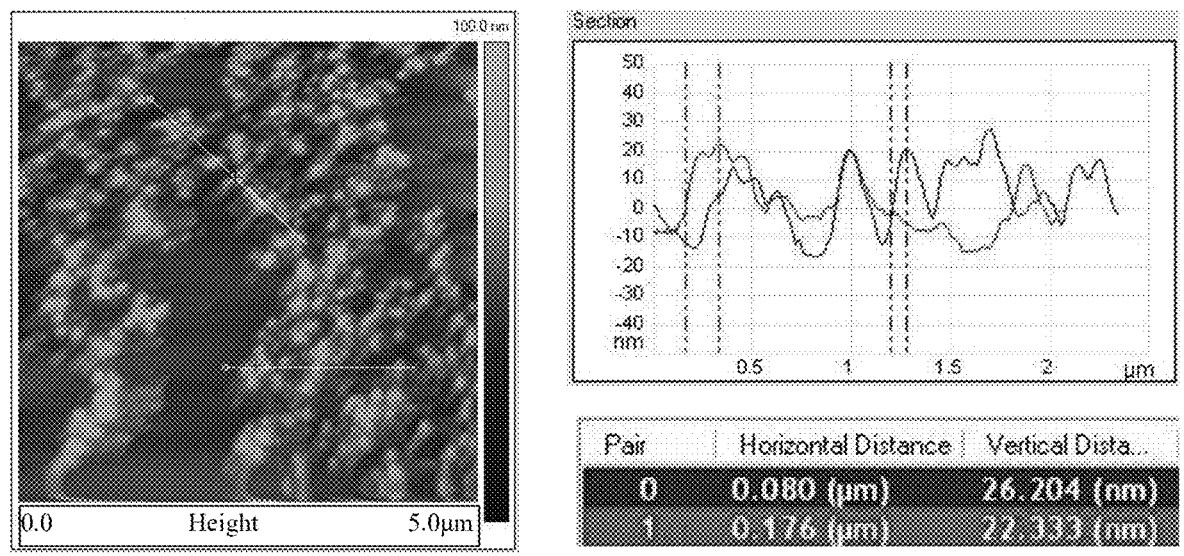
FIG. 8 shows AFM micrograph of particles loaded with 0.01% Mometasone furoate, according to example 1D, which indicate that Mometasone furoate loaded particles show spherical shape with narrow size distribution in the range between 15 and 35 nm. The particles are dispersed separately with no tendency to form aggregates.
Figure 9:
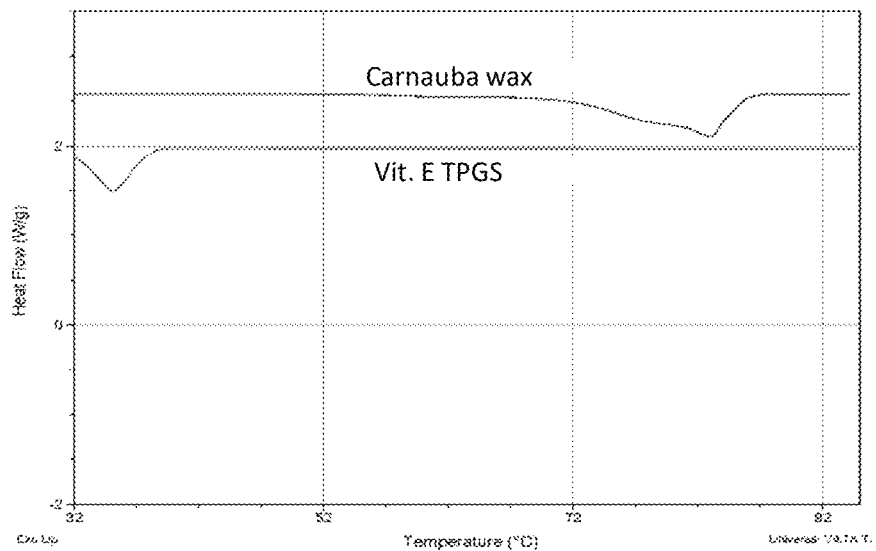
FIG. 9 shows TMDSC of row carnauba wax and TPGS, according to example 1 with their characteristic isotherms.
Figure 10:
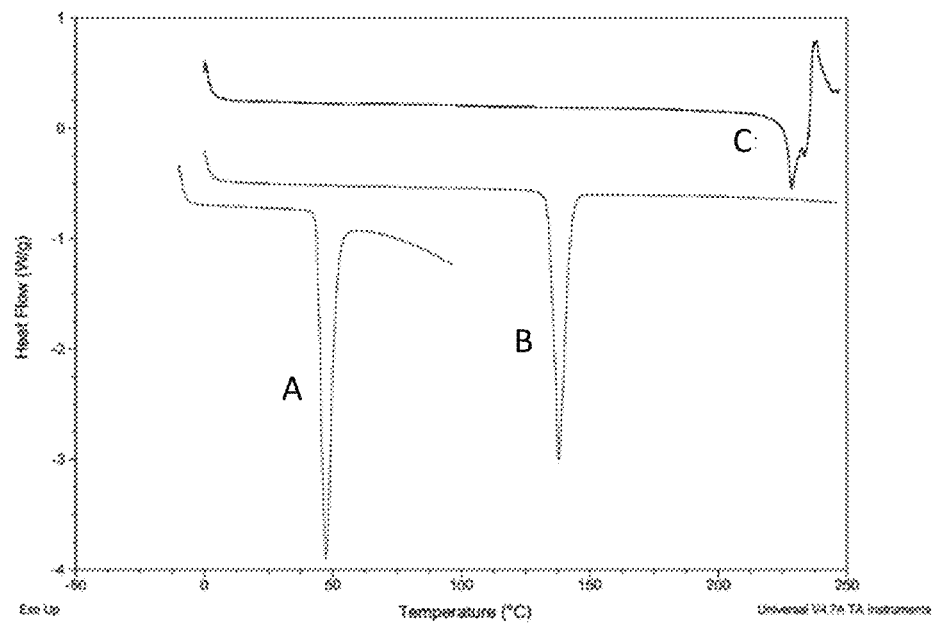
FIG. 10 shows TMDSC of row Menthol (A) Loratadine (B) and Mometasone furoate (C), according to example 1 with their characteristic isotherms.
Figure 11:
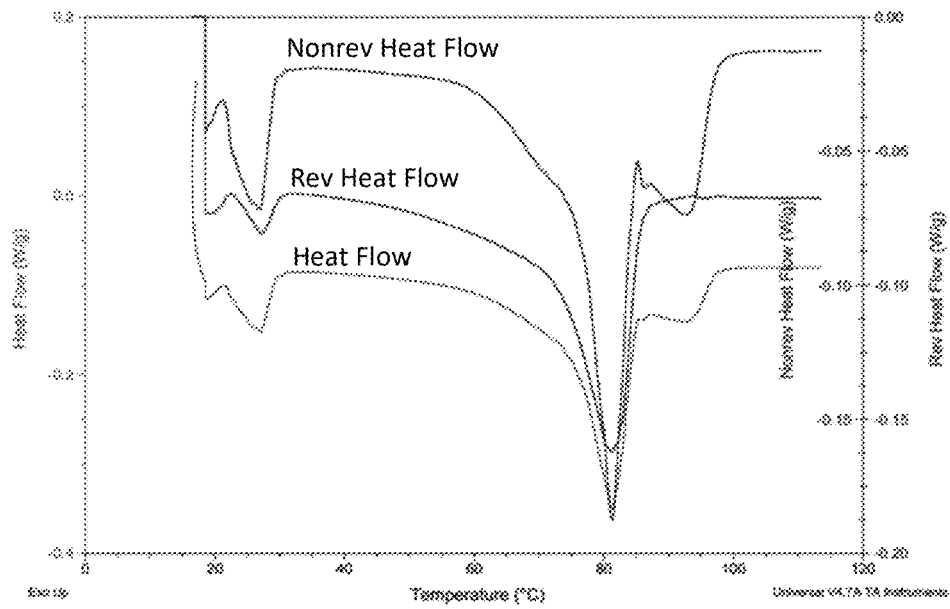
FIG. 11 is TMDSC of 0.1% Menthol lipid particles, according to example 1. The results show that after loading on the SLNs in appropriate concentrations, active substances' melting peaks disappear. This is thought to be related either with their amorphization in result of molecule dispersion within the lipid matrix.
Figure 12:
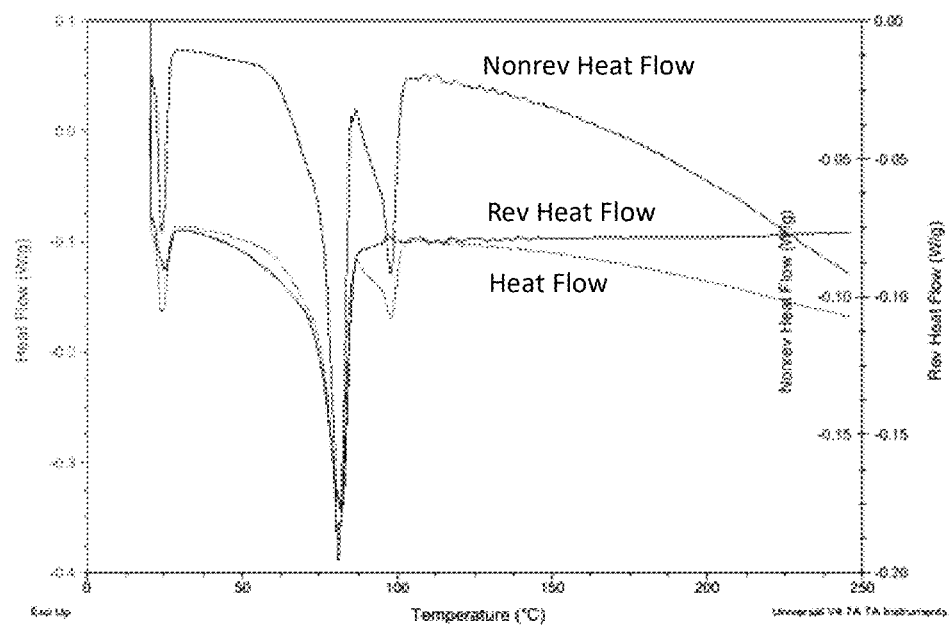
FIG. 12 is TMDSC of lipid particles loaded with 0.01% Mometasone furoate and 0.1% Loratadine, according to example 1F. The results show that after loading on the SLNs in appropriate concentrations, active substances' melting peaks disappear. This is thought to be related either with their amorphization in result of molecule dispersion within the lipid matrix or dissolution of Loratadine in the liquefied lipid at temperatures above 82° C.
Figure 13:
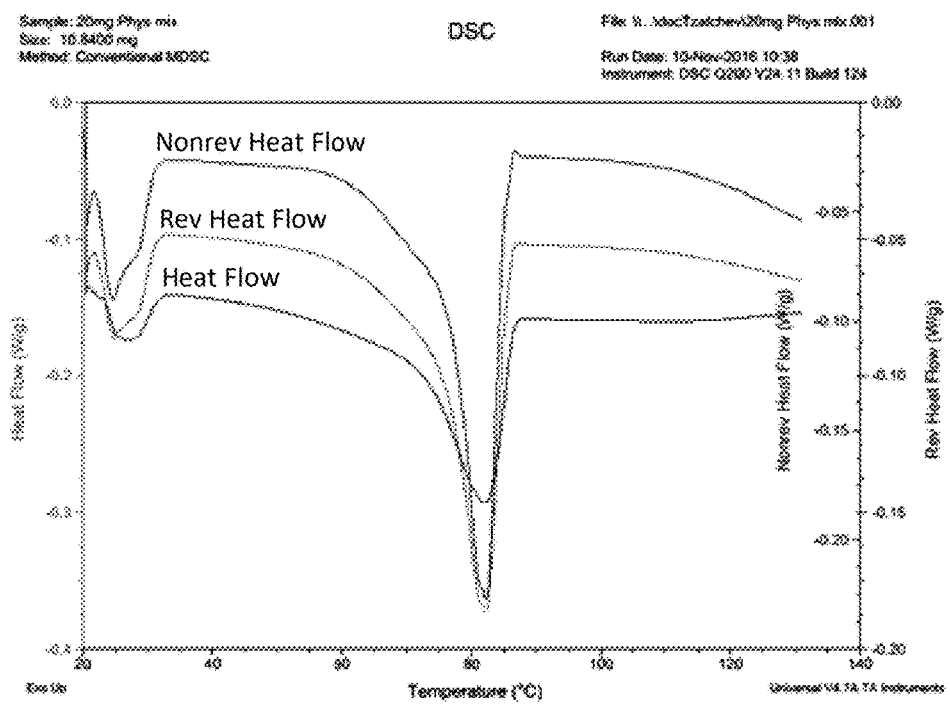
FIG. 13 represents TMDSC of physical mixture of the particle composition, according to example 1G. The heat flow shows lack of characteristic Loratadine isotherm. This is thought to be related with dissolution of Loratadine in the liquefied lipid at temperatures above 82° C.
Figure 14:
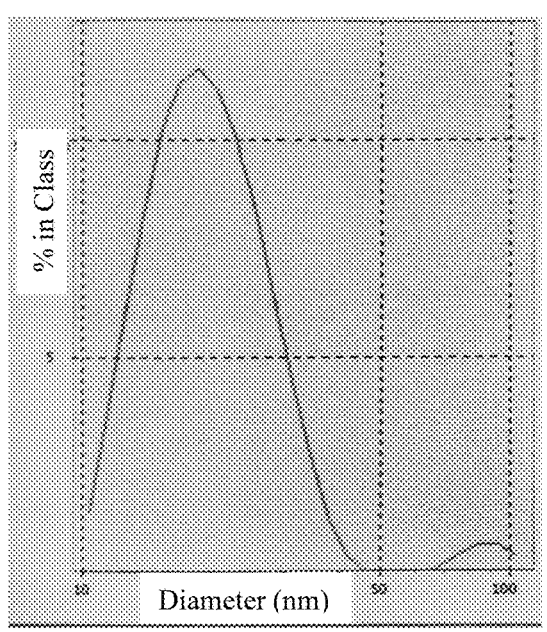
FIG. 14 DLS graph of particle size distribution of composition 1A.
Figure 15:
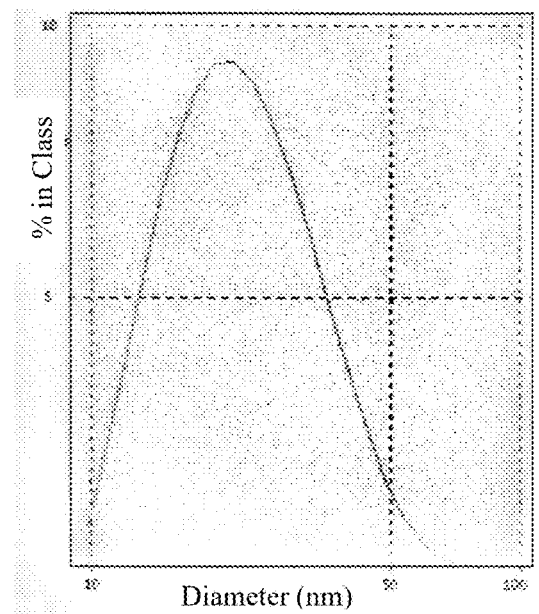
FIG. 15 shows DLS graph of particle size distribution of composition 1A'.
Figure 16:
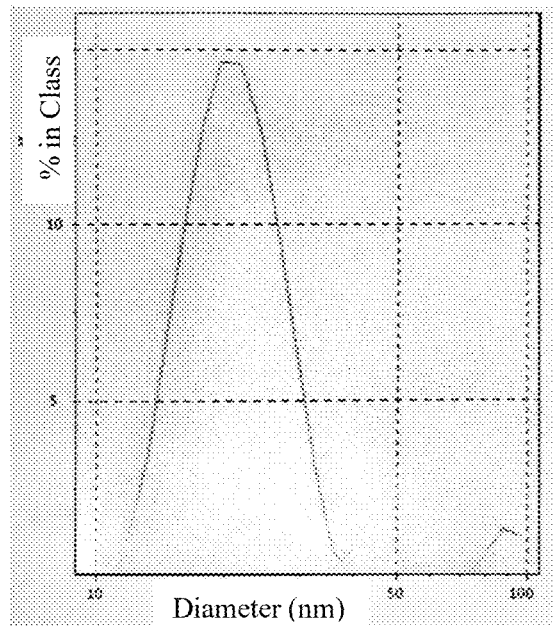
FIG. 16 shows DLS graph of particle size distribution of composition 1D.
Figure 17:
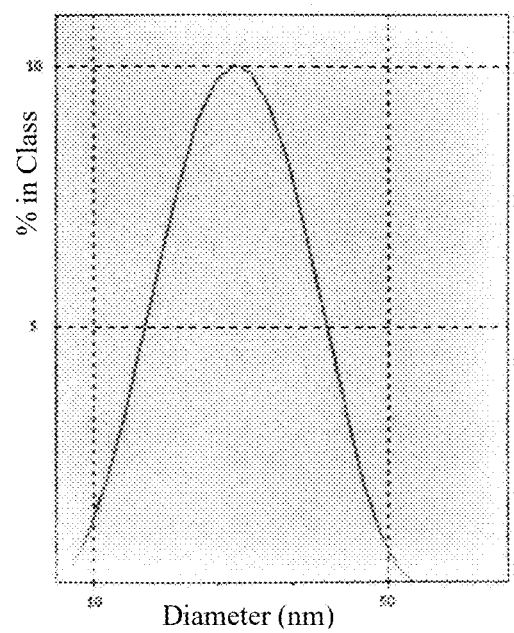
FIG. 17 shows DLS graph of particle size distribution of composition 1D'.

The tested samples of placebo (example 1A, FIG. 6), 0.01% (example 1D, FIG. 7) and 0.03% (example 1E, FIG. 8) Mometasone furoate loaded particles show spherical shape with narrow size distribution in the range between 15 and 35 nm. The particles are dispersed separately with no tendency to form aggregates.

C. Temperature modulated differential scanning calorimetry (TMDSC) was performed on DSC apparatus Q200, TA instruments, USA. The temperature calibration was performed with sapphire disc supplied by TA instruments in Tzero aluminum pans (TA instruments) in the desired temperature interval.

Row ingredients and compositions 1C, 1F and 1G were scanned (FIGS. 9-13). The samples were freeze-dried and desiccated until testing. The samples were tested in the Tzero pans from 20° C. to 250° C. with 2° C./min heating rate, modulation amplitude 1° C. and a period of 60 seconds under nitrogen flow (50 mL/min).

The results indicate that after loading on the SLNs in appropriate concentrations, active substances' melting peaks disappear. This is thought to be related either with their amorphization in result of molecule dispersion within the lipid matrix or dissolution of Loratadine in the liquefied lipid at temperatures above 82° C.

Study of Z Average and Polydispersity by Dynamic Light Scattering (DLS)

The DLS analyses were performed on Zetasizer Nano ZSP, Malvern Instruments, England and Malvern 4700 C, Malvern Instruments, England.

A. Analysis of Freshly Prepared Samples.

The analysis was performed on fresh not filtered samples from compositions 1A, 1B, 1C, 1D. The particle size of the tested samples varies between 29.4 and 32.8. The results of size, polydispersity and z-potential of tested SLNs dispersions received are indicated in the Table 2.

TABLE 2

Size, polydispersity and z-potential of tested SLNs dispersions

| Measured components | 1A | 1A' | 1B | 1C | 1D | 1D' |
|---|---|---|---|---|---|---|
| Size (nm) | 32.8 | 30.8 | 29.4 | 33.6 | 30.9 | 27.8 |
| Polydispersity | 0.399 | 0.452 | 0.255 | 0.321 | 0.398 | 0.375 |
| Z potential (mV) | −18.5 | — | −33.5 | −30.4 | — | — |

"—" - mean "not tested"

The size and % distribution of tested SLNs dispersions of the laboratory technology produces particles with bimodal size distribution are indicated in Table 3. The yield of the particles with size range between 20 nm and 30 nm (peak 1) is over 95%.

TABLE 3

The size and % distribution of tested SLNs dispersions of the laboratory technology produces particles with bimodal size distribution

| Sample | Size distribution | % distribution |
|---|---|---|
| 1A | Peak 1: 20.3 nm | Peak 1: 97.7 |
|  | Peak 2: 87.6 nm | Peak 2: 2.3 |
| 1D | Peak 1: 21.1 nm | Peak 1: 96.9 |
|  | Peak 2: 90.1 nm | Peak 2: 3.1 |

B. Analysis of Samples after Filtration

Samples from compositions from Examples 1A, 1B and 1C were analysis after filtration trough filter 0.22 μm. Filtered samples have narrower size distributed in monomodal pattern.

The results of the analysis of size and polydispersity after filtration trough 0.22 μm filter are indicated in the Table 4.

TABLE 4

The results of the analysis of size and polydispersity after filtration trough 0.22 μm filter

| Measured parameters | 1A | 1B | 1C | 1D |
|---|---|---|---|---|
| Size(nm) | 19.3 | 22.2 | 22.6 | 18.5 |
| Polydispersity | 0.0117 | 0.0045 | 0.0088 | 0.0108 |

C. Analysis of Samples after Incubation with Pancreatic Lipase

Samples 1A, 1A', 1D and 1D' were compared. After preparation samples 1A' and 1D' were incubated at 37° C. for 24h before testing.

A slight size reduction was observed in 1A' and 1D' when compared with the corresponding sizes of 1A and 1D (see Table 2 and FIGS. 14-17). A lack of the second peak at both samples 1A' and 1D' was also detected. Probable explanation for the noted differences can be found in the difference in produced lot quantities: 1A and 1D were prepared each in 50.00 g dose; 1A' and 1D' were prepared each in 200.00 g dose, and had undergone slower cooling of the hot microemulsion at stage C of their production.

D. Formation of Protein Corona

The test was conducted to study the possible affinity of the SLNs of the present invention to form protein corona with bovine serum albumin (BSA). Formation of protein corona is a sign of affinity of particles to adsorb body proteins. Such complexes possess different ability to move through membranes due to increased size and changed surface structure and charge. Also, particles with protein corona can become immunogenic. Lipid nanoparticles generally have the affinity to form protein corona with soluble body proteins.

Methodology

The experiment was conducted with sample 1A. 5 ml of dispersion 1A was added to 25 ml volumetric flasks inscribed "1A" and another 5 ml of dispersion 1A was added to a 25 ml volumetric flask inscribed "1A+BSA" respectively. Flask 1A was diluted to the mark with ultrapure water and homogenized; 5% w/v solution of bovine serum albumin in ultrapure water was added to the mark of the flask 1A+BSA, homogenized and incubated at 37° C. for 2 hours before the test.

The results are shown in table 6. No protein corona was detected. The slight increase in particle size in sample 1A+BSA with less than 1 nm here is thought to be influenced by the slight increase in viscosity of the 1A+BSA. Thus, the determination based on the DLS analysis result in a bigger hydrodynamic diameter corresponding to the slower fluctuations of the particles in the more viscous medium.

The determination of frequency shifts and ensuing calculation to obtain particle size in the DLS analysis is based on the Stokes-Einstein equation: $D_H = kT/3\pi\eta D$ $D_H$=hydrodynamic diameter
k=Boltzmann constant
T=absolute Temperature
η=dynamic viscosity
D=Diffusion coefficient The lack of protein corona in spite of the negative charge of the particles can be explained with the high lipophilicity of the SLNs and steric stabilization by the surfactants (TPGS; polysorbate 40).

E. Stability Studies

Stability was studied with respect to tendency of aggregates formation. Changes in particle size were studied over a period of 24 months. Samples from compositions 1A and 1D were prepared and to each were added 0.5% EDTA disodium salt as a microbial preservative. Samples were filtered through 0.22 μm filter and filled in brown glass bottles and stored in dark place at room temperature. Samples were tested on the $0^{th}$, $12^{th}$ and $24^{th}$ month.

The results from Size and polydispersity index of tested SLNs dispersions are indicated in the Table 5.

TABLE 5

The results from Size (polydispersity) of tested SLNs dispersions

| Sample | $0^{th}$ month | $12^{th}$ month | $24^{th}$ month |
|---|---|---|---|
| 1A | 19.3 (0.352) | 19.9 (0.364) | 21.4 (0.373) |
| 1D | 18.5 (346) | 19.4 (0.355) | 21.3 (0.358) |

The results indicate neglible increase in particle size in both tested samples with time. No aggregates were formed during the test period.

Entrapment Efficiency and In-Vitro Dissolution Kinetics

1. Entrapment Efficiency

A. The Entrapment efficiency relates to the % drug that is successfully entrapped into nanoparticles. It is calculated as follows: % EE=[(Drug added−Free "unentrapped drug")/Drug added]*100.

Methodology

The test is conducted with freshly prepared, not filtered composition 4D. 5 ml of the tested dispersion were placed in a Dialysis Membrane Tubing 3500 Dalton MWCO 10 mm diameter and 80 mm long, pre-hydrated for 24 h. The membrane is permeable for the active substance, but not for the particles. The membrane is gently folded and placed into 15 ml centrifuge tube and pinched with the polypropylene cap. The samples are centrifuged at 2000×rpm for 20 min. Aliquots from the filtrate were analysis on Cary UV-Vis spectrophotometer, Agilent Technologies for Mometasone furoate content according to a developed analytical method.

The % EE is 98.8.

B. Active substance loading

The drug loading relates to the maximum amount of the active substance, % that can be incorporated into the nanoparticles.

Methodology

Cary UV-Vis spectrophotometer, Agilent Technologies was used for determination of Mometasone furoate content according to a developed analytical method.

Series of compositions derived from composition 1D with concentration of the loaded active substance ranging from 0.0025% w/w/ to 0.0200% w/w were used for the experiment.

| Compounds | 1D1 | 1D2 | 1D3 | 1D | 1D4 | 1D5 | 1D6 | 1D7 |
|---|---|---|---|---|---|---|---|---|
| Carnauba wax | | | | | 1.00 | | | |
| Red palm oil concentrate (30% tocotrienols) | | | | | 0.2 | | | |
| d-α-Tocopheryl polyethylene glycol 1000 succinate (TPGS) | | | | | 0.5 | | | |
| Polysorbate 40 | | | | | 0.7 | | | |
| Mometasone furoate | 0.0025 | 0.0050 | 0.0075 | 0.01 | 0.0125 | 0.0150 | 0.0175 | 0.0200 |
| Water | | | | to 100 | | | | |

Figure 18:
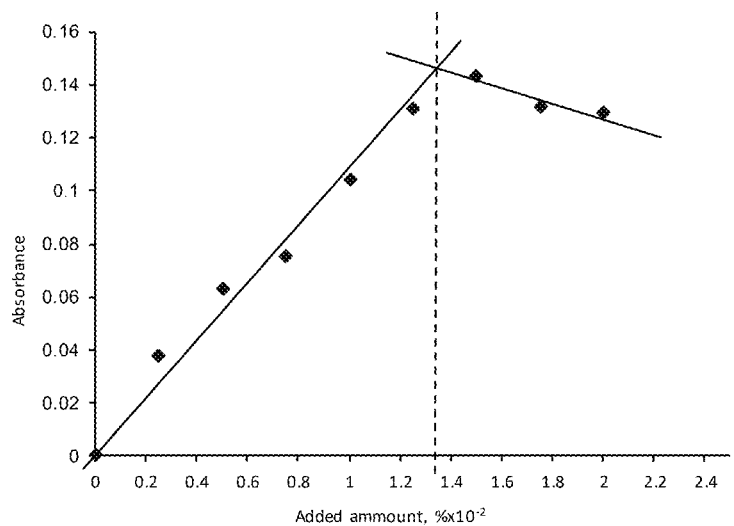
FIG. 18 is a plot of added amount Mometasone furoate to the SLNs against measured absorption with determination of the maximum amount of the active substance in % that can be incorporated into the nanoparticles (i.e. loading capacity).

Mometasone furoate have water solubility 0.00523 mg/mL, which makes it practically insoluble. The compositions were prepared according to the technology, described in example 2. After obtaining the samples were stored for 24 h in refrigerator at 4° C. to allow equilibrium between dissolved/undissolved states of Mometasone furoate to be reached. Before analysis the samples were filtered through 0.45 μm filter. The samples were diluted appropriately if necessary and the absorption spectra were taken. The used concentrations were plotted on a graph against the measured absorptions (FIG. 18). The system reaches equilibrium at $1.34 \times 10^{-2}$% which well corresponds with the visual change of the dispersions with the appearance of sediment in concentrations of $1.5 \times 10^{-2}$% and above.

2. Dissolution of 0.01% Mometasone Furoate Loaded Particles According to 1D.

This example gives another demonstration of the ability of SLNs of the present invention to keep the encapsulated substance "locked" without releasing it in an in-vitro dissolution experiment. In a separate experiment, the influence of added pancreatic lipase on the drug release was investigated. The tests were designed for the purpose and consist of a donor phase of the particle suspension loaded with active substance and acceptor phase, separated with a dialysis membrane.

Methodology

In separate experiments the test was conducted with freshly prepared not filtered compositions 1D and 1D'. 5 ml of the tested dispersion were placed in a Dialysis Membrane Tubing 3500 Dalton MWCO 10 mm diameter and 80 mm long, pre-hydrated for 24 h. The membrane is permeable for the active substance, but not for the particles and lipase. The membrane is sealed both sides and submerged in a beaker glass with 250 ml ultrapure water with 0.1% Polysorbate 40 under constant steering and thermostated at 37° C. Samples were collected at 0 min, 15 min, 30 min, 60 min, 120 min, 240 min, 480 min, 960 min, and 1440 min. The samples were evaporated under nitrogen and the residue dissolved in methanol. The obtained solutions were analysis on Cary UV-Vis spectrophotometer, Agilent Technologies.

The kinetic study (FIG. 19) shows extremely low release profile for both the tested compositions. The lipase treated composition shows slightly higher release. At the 24h released Mometasone from 1D and 1D' was 2.2% resp. 4.1%. These values are thought to origin both from the very low dissolution profile of the particles and from the free/unincluded Mometasone furoate.

Example 2. Particles Internalization into Cells

This experiment was built on the hypothesis that if the particle does not release the dye trough passive diffusion or leak, the only way the dye to meat and form a fluorescent complex with cell RNA is by particle enzymatic erosion and free dye release.

To do this experiment the yeast *Saccharomyces cerevisiae* (*S. cerevisiae*) has been chosen as one of the most widely used eukaryotic model organisms.

Dye Thiazole orange (TO) derivative with high affinity to form fluorescent complexes with RNA was synthesized for the purpose. The dye is highly lipophilic and once loaded in the SLNs, or solubilized, it's is not fluorescent. Due to its positive charge the dye is not permeable through the cell wall. The only way the dye can enter the cell is to be loaded on a transport carrier, such as SLNs. The ways of SLNs internalization into the cells is by diffusion through the cell pores by endocytosis.

The experiment is also informative for possible leak or passive diffusion of the dye from the SLNs. Such pre-internalization release should result in fluorescence incidents outside the cells with RNA secreted with exosomes. Secretion of extracellular vesicles is part of the physiology of *Saccharomyces cerevisiae*.

TO analogues do not fluoresce in the free state in solution. Fluorescence arises when rotation about the monomethine bridge between the two heterocyclic moieties is somehow restricted [Carlsson, C.; Larsson, A.; Jonsson, M.; Albinsson, B.; Norden, B. *The Journal of Physical Chemistry*, 1994, 98, 10313-21.]. Such a restriction occurs when TO derivatives bind to nucleic acids by intercalation between the base pairs [Netzel, T. L.; Nafisi, K.; Zhao, M.; Lenhard, J. R.; Johnson, I. *The Journal of Physical Chemistry*, 1995, 99, 17936-47; Nygren, J.; Svanvik, N.; Kubista, M. *Biopolymers*, 1998, 46, 39-51.] or presumably between individual bases in single-stranded nucleic acids and in both cases a dramatic increase of the fluorescence is observed.

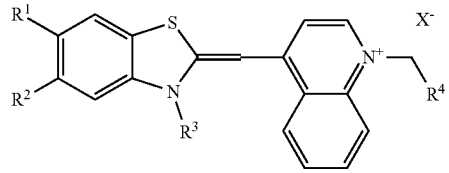

For the present test Thiazole orange analogue was used were $R^1$, $R^2$, $R^3$ and $R^4$ are alkyl or substituted alkyl.

To understand the reason for the observed fluorescence in the cell's cytoplasm an in vitro experiment was made with the TO analog in the absence and in the presence of salmon sperm double stranded DNA (dsDNA) and transfer RNA (tRNA) from bovine liver (Sigma-Aldrich).

Figure 19:
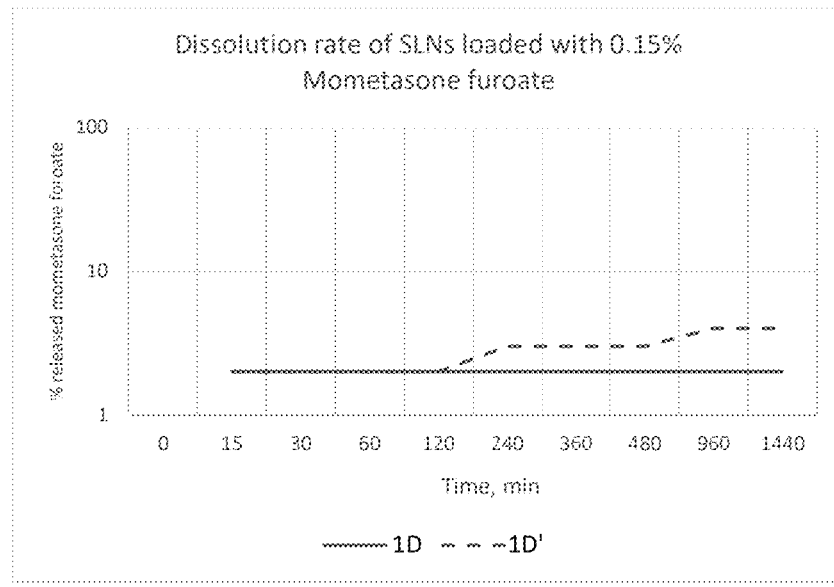
FIG. 19 represents Mometasone furoate release from SLNs. The kinetic study shows extremely low release profile for both the tested compositions. The lipase treated composition shows slightly higher but still neglible release.
Figure 20:
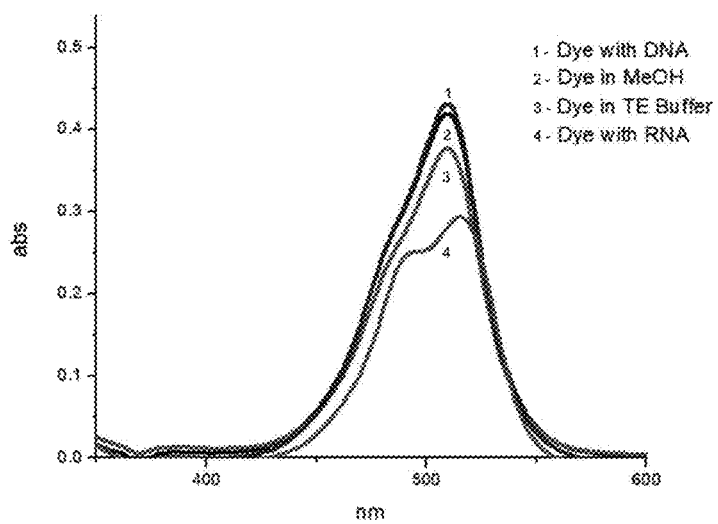
FIG. 20 shows absorption of the dye in methanol and TE buffer (conc. of the dye 1.10-5 M, conc of the nucleic acids 4 mkM).

The absorption of the dye in methanol and TE buffer (conc. of the dye $1.10^{-5}$ M, conc of the nucleic acids 4 mkM) is indicated in FIG. 19 and the fluorescence spectra of Thiazole orange analog free in TE buffer, in presence of DNA and in presence of RNA is indicated in FIG. 20

It was demonstrated that the dye is highly specific to RNA.

Tested Compositions

Particles loaded with fluorescence dye in the following compositions:

| Compound | Amount (w/w parts) |
|---|---|
| A. Solubilizate of dye | |
| Polysorbate 40 | 0.70 |
| DYE | 0.00001 |
| Water | to 100.00 |
| B. Particles, loaded with dye | |
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| DYE | 0.00001 |
| Water | to 100.00 |

Methodology

The particles were obtained according to the procedure according to Example 1.

*Saccharomyces Cerevisiae* cells were cultured in Dulbecco's Modified Eagle Medium (DMEM) supplemented with 10% fetal bovine serum (FBS) and 100 units/ml penicillin and 100 µg/ml streptomycin at 37° C. and 5% CO2. For micro-irradiation and image acquisition cells were plated in MatTek glass bottom dishes (~40% confluence), then cultured for 24h, washed with PBS and supplemented with 2 ml FluoroBrite DMEM medium containing 10% FBS and 2 mM GlutaMAX. Before imaging 100 µl lipid particles was added. Image acquisition was performed on an Andor Revolution system using Nikon 60× (NA1.2) water immersion objective and iXon897 EMCCD camera. Images were acquired in two channels—488 nm laser excitation in 7 Z planes with 0.5 µm plane spacing and single plane in bright-field DIC.

Figure 27:
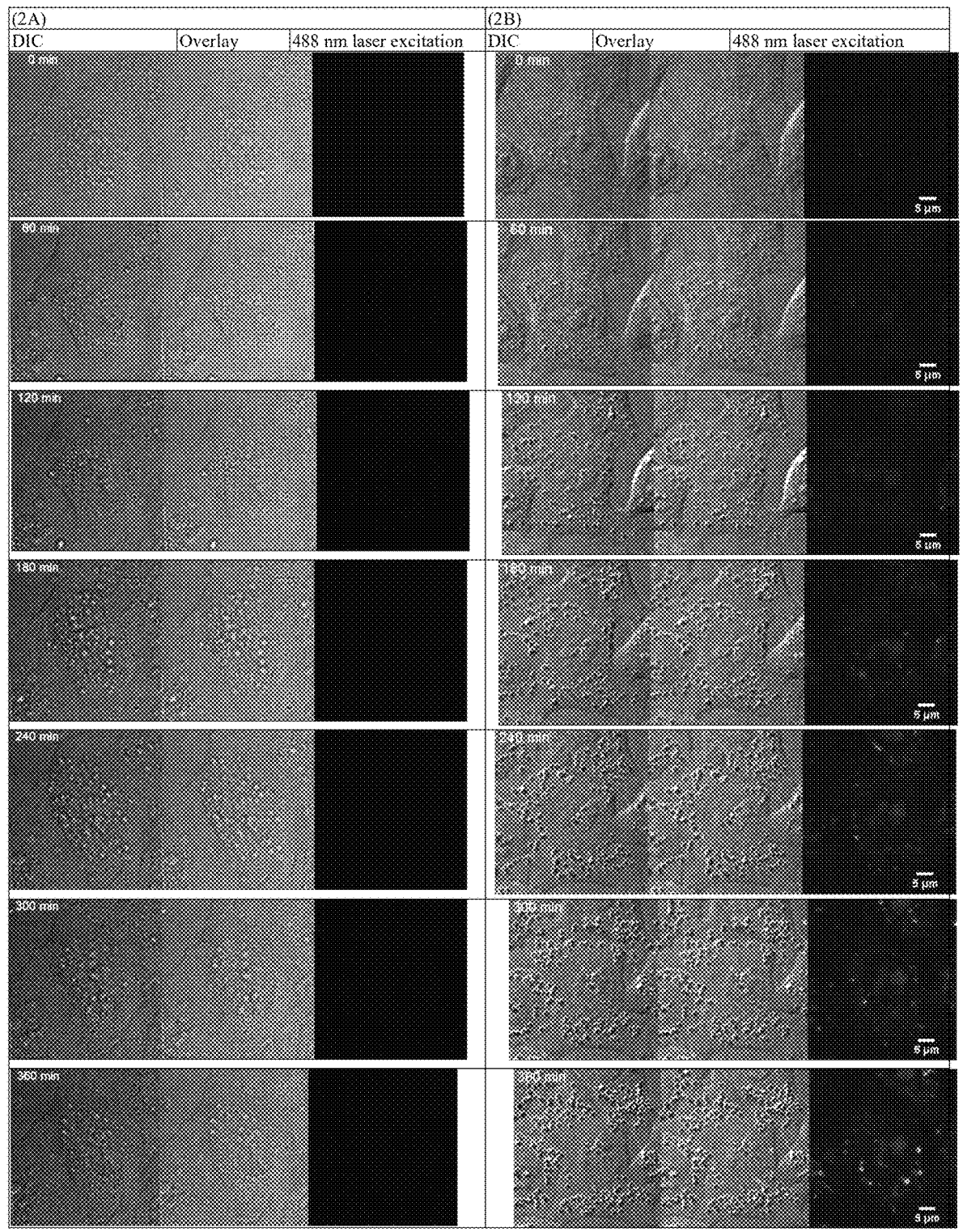
FIG. 27 and FIG. 27A illustrate of cell internalization of SLNs loaded with fluorescence dye. Micrographs of *Saccharomyces cerevisiae* cells treated with dye solubilizate (2A) and dye loaded in SLNs (2B) according to example 2
Figure 27A:
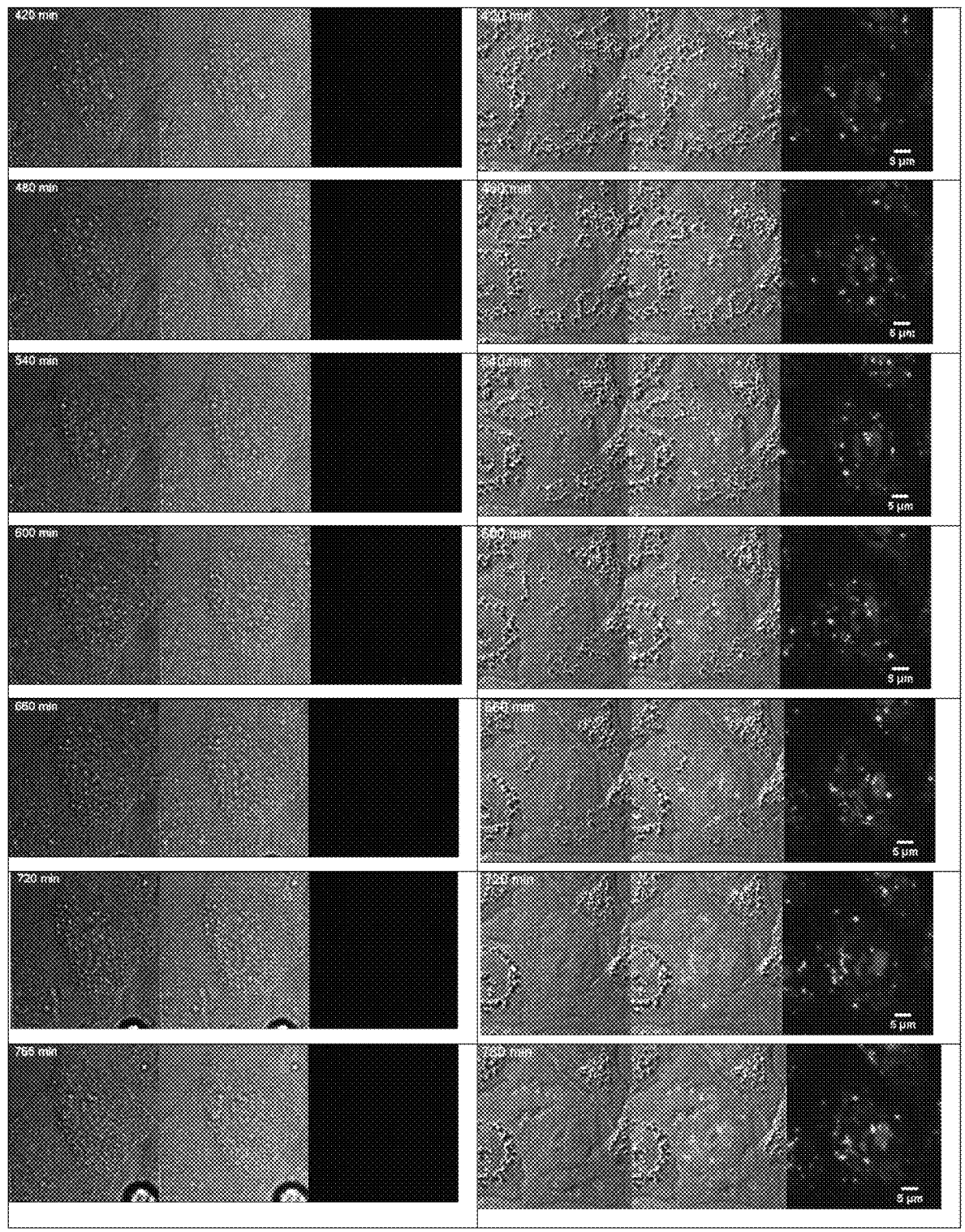

The dye has been synthesized for the purpose and possesses high lipophilicity and strong emission after binding to nucleic acids. The captures from defined time points up to the end of the experiment ($13^{th}$ h) are presented in FIG. 27 and FIG. 27A The dye solubilizate gives very low diffuse emission with no detected emission spots within the examined cells. The absence of emission is illustrative for inability of the dye to enter the cell in spite of the presence of polysorbate 80, known solubilizer and absorption enhancer (see picture set 2A). Solubilizate also doesn't give extracellular fluorescent complexes with RNA most probably because of molecule associations within surfactant micelles rather than free incorporated molecules. As can be observed from the picture set in column 2B, 60 min after the addition of nanoparticle suspension, the fluorescence within cells progressively increased until the end of the experiment (13 hours). As far the emission time is limited (less than millisecond) in result of the fluorescence decay the increasing intensity of the recorded multiple light spots (incidents) within the *Saccharomyces cerevisiae* cells and the lack of fluorescence outside the cell walls can be explained with slow particle enzymatic degradation and subsequent free dye release. No pre-internalization dye release was detected.

Example 3. Safety and Toxicity Evaluations

1. Toxicity on Cells

The spontaneously immortalized human HaCaT keratinocyte cell line was maintained in a 70% monolayer culture in a Dulbecco's Modified Eagle's Medium (DMEM-F12; Lonza) supplemented with 10% fetal bovine serum (FBS; Lonza). Both cell lines were maintained in a humidified atmosphere containing 5±1% CO2 in air (standard culture conditions) at 37° C.

Samples 1G, 2A and 2B have been tested. The cytotoxicity of the lipid nanoparticles was assessed following 30 min exposure and staining with Trypan blue using a Countess Automated cell counter (Invitrogen).

All tested samples showed no observable effects on viability of HaCaT cells. Interestingly, the increase in lipid concentration from 1% to 5% (1A to 2A) led to a decrease in toxicity on HaCaT cells. A possible explanation can be related with antioxidant and nutritive value of the lipid composition.

Additional Tested Simple have the Following Compositions:

| 3A. Placebo (5% lipid phase) | |
| --- | --- |
| Compounds | Amount (w/w parts) |
| Carnauba wax | 5.00 |
| Red palm oil concentrate (30% tocotrienols) | 1.00 |
| d-α-Tocopheryl polyethylene glycol 1000 succinate (TPGS) | 2.50 |
| Polysorbate 40 | 3.50 |
| Water | To 100.00 |

| 3B. 0.1% Loratadine (6% lipid phase) | |
| --- | --- |
| Compounds | Amount (w/w parts) |
| Carnauba wax | 5.00 |
| Red palm oil concentrate (30% tocotrienols) | 1.00 |
| d-α-Tocopheryl polyethylene glycol 1000 succinate (TPGS) | 2.50 |
| Polysorbate 40 | 3.50 |
| Loratadine | 0.1 |
| Water | To 100.00 |

Viability cell count (HaCaT) after 30 min incubation with different formulations are indicated in FIG. 20.

Example 4. Evaluation of Nasal Epithelium Safety/Toxicity

As far as all the ingredients in the composition of the particle core of the present invention are Pharmacopeial (EP, USP) and/or GRASS listed by FDA, the possible toxicity and/or safety concerns can arise from the particle size itself and from the expected high intracellular drug concentrations. Nasal mucosa has been chosen as a potential place for application of the SLNs of the current invention and for its delicate structure.

Animals

The use of animals in example 4 was authorized by the Local Animal Ethics Committee at veterinary faculty of Trakia University, Stara Zagora, Bulgaria, with protocol 38/05.12.2013. Ten male and ten female healthy New Zealand rabbits were selected. The temperature in the room was kept in the range 20° C.+/−2° C. The animals were fed on standardized normal diet, water ad libitum and kept in individual cages. Seven days for adaptation were given to the animals after their receiving. At the beginning of the tests the weight of males was 3.248±0.321 kg and the weight of the females 3.452±0.483 kg.

The animals were divided in three groups:
group A (4 males and 3 females) was treated with Allergodil nasal spray;
group B (4 females and 3 males) with the test formulation LORNP;
group C (3 males and 3 females) was treated with sodium chloride sol 0.9%, 100 μl of the respective formulation was sprayed daily into the left nostril for 30 days. The right nostril was left untreated.

At the day of the last administration all animals were anaesthetized with i.m. injection of ketamine (35 mg/kg) and xylazine (5 mg/kg).

Biopsy samples from the left and right nostrils were obtained using a 2 mm punch biopsy needle from the lateral wall of the rostral portion of the dorsal nasal meatus, which corresponds to the approximate area of the sprayed drug.

The preparations were fixed in 10% neutral buffered formalin. The tissue samples were then processed routinely and imbedded in paraffin blocks. Tree-micron-thick sections were sliced, mounted on glass slides and stained with hematoxylin and eosin (H&E). The biopsy samples from the untreated right nostrils served as control in each experimental group. The slides were examined under light microscope. Each slide was inspected for integrity and presence of pathological alterations associated with irritation and toxicity the epithelial and sub-epithelial layers confined in the samples.

Figure 21:
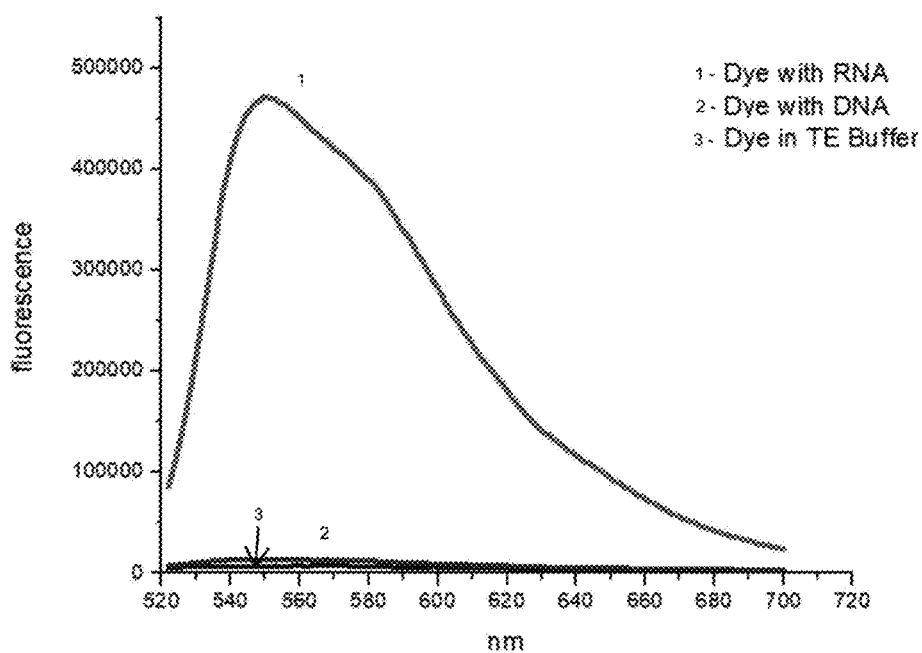
FIG. 21 shows fluorescence spectra of Thiazole orange analog free in TE buffer, in presence of DNA and in presence of RNA.

Microscopy evaluation of nasal biopsy samples from treatment groups A, B and C in the samples from each group were presented from normal wavy and slightly keratinized squamous stratified epithelium (FIG. 21) and small portions of transitional pseudo stratified ciliated epithelium (not shown). The sub-epithelial layer consisted of loose connective tissue with occurrence of numerous cavernous veins and tubular serous glands supported by a hyaline cartilage.

The microscopic examination of biopsies showed no pathological changes in the nasal epithelial membrane and its adjacent layers in any sample. When the samples were compared no significant difference was detected in the findings between treatment groups.

Light photomicrographs of cross-sections from biopsy samples of treatment groups A, B and C., FIGS. (21*a*), (21*b*), (21*c*) from the right (R) and left (L) nasal vestibules, demonstrating the presence normal stratified squamous epithelium. Respectively 21a L×400; 21a R×260; 21b L 260×; 21b R360; 21c L×360 and 21c R×300; bar 1 cm; H&E.

Example 5. Evaluation of Eye Safety/Toxicity

The eye test was conducted to test the safety of the SLNs on eye tissues integrity. The Draize test was used as well established for evaluation of toxicity of chemical agents. The specificity of the current experiment is that all the ingredients of the compositions are well studied for local toxicity, they are Pharmacopeial (EP, USP) and/or Grass listed by FDA, and so the test aims to evaluate the safety of the particle size.

A. Draize Test

Draize test is internationally recognized for estimation the local toxicity and uses standardized protocol for instilling agents onto the cornea and conjunctiva of laboratory animals. A sum of ordinal-scale items of the outer eye gives an index of ocular morbidity. The test serves to study the integrity and condition of the eye after exposure to examined agent and is based on "activation" of fluorescein by damaged tissue.

24h before the experiment the condition of eyes of all animals were inspected.

Two males and one female animal received single dose of 100 µl particle dispersion according to example 3B in the right eye. Both eyes of the animals were inspected at 24, 48 and 72 hours intervals and rated according to the scale in table 6.

No observable changes in rabbit cornea, conjunctiva or iris have been observed.

B. Modified Draize Test 24h before the experiment the condition of eyes of all animals were inspected.

Three male and three female animals received 100 µl particle dispersion, according to example 3B in the right eye on a daily manner for 14 days. Both eyes were inspected at 24, 48 and 72 hours intervals after the last treatment and rated according to the scale in table 6.

No observable changes in rabbit cornea, conjunctiva or iris have been observed.

TABLE 6

Evaluation of symptom score according to the
"Scale of Weighted Scores for Grading
the Severity of Ocular Lesions" *

| Group | | Single treatment | | | | 14 days treatment | | | | |
|---|---|---|---|---|---|---|---|---|---|---|
| Animal | | 1 | 2 | 3 | 4 | 5 | 6 | 7 | 8 | 9 |
| 24 h after last administration | | | | | | | | | | |
| I. Cornea | A: | 0 | 0 | 0 | 0 | 0 | 0 | 0 | 0 | 0 |
| | B: | 0 | 0 | 0 | 0 | 0 | 0 | 0 | 0 | 0 |
| II. Iris | A: | 0 | 0 | 0 | 0 | 0 | 0 | 0 | 0 | 0 |
| III. Conjunctiva | A: | 0 | 0 | 0 | 1 | 0 | 0 | 0 | 1 | 0 |
| | B: | 0 | 0 | 0 | 0 | 0 | 0 | 0 | 0 | 0 |
| | C: | 0 | 0 | 0 | 0 | 0 | 0 | 0 | 0 | 0 |
| 48 h after last administration | | | | | | | | | | |
| I. Cornea | A: | 0 | 0 | 0 | 0 | 0 | 0 | 0 | 0 | 0 |
| | B: | 0 | 0 | 0 | 0 | 0 | 0 | 0 | 0 | 0 |
| II. Iris | A: | 0 | 0 | 0 | 0 | 0 | 0 | 0 | 0 | 0 |
| III. Conjunctiva: | A: | 0 | 0 | 0 | 1 | 0 | 0 | 0 | 0 | 0 |
| | B: | 0 | 0 | 0 | 0 | 0 | 0 | 0 | 0 | 0 |
| | C: | 0 | 0 | 0 | 0 | 0 | 0 | 0 | 0 | 0 |

TABLE 6-continued

Evaluation of symptom score according to the
"Scale of Weighted Scores for Grading
the Severity of Ocular Lesions" *

| Group | | Single treatment | | | | 14 days treatment | | | | |
|---|---|---|---|---|---|---|---|---|---|---|
| 72 h after last administration | | | | | | | | | | |
| I. Cornea: | A: | 0 | 0 | 0 | 0 | 0 | 0 | 0 | 0 | 0 |
| | B: | 0 | 0 | 0 | 0 | 0 | 0 | 0 | 0 | 0 |
| II. Iris | A: | 0 | 0 | 0 | 0 | 0 | 0 | 0 | 0 | 0 |
| III. Conjunctiva | A: | 0 | 0 | 0 | 0 | 0 | 0 | 0 | 0 | 0 |
| | B: | 0 | 0 | 0 | 0 | 0 | 0 | 0 | 0 | 0 |
| | C: | 0 | 0 | 0 | 0 | 0 | 0 | 0 | 0 | 0 |

TABLE 7

Scale of Weighted Scores for Grading the Severity of Ocular Lesions

| Lesion | Score[1] |
|---|---|
| Cornea | |
| A. Opacity-Degree of density (area which is most dense is taken for reading) | |
| Scattered or diffuse area-details of iris clearly visible | 1 |
| Easily discernible translucent areas, details of iris slightly obscured | 2 |
| Opalescent areas, no details of iris visible, size of pupil barely discernible | 3 |
| Opaque, iris invisible | 4 |
| B. Area of cornea involved | |
| One quarter (or less) but not zero | 1 |
| Greater than one quarter but less than one half | 2 |
| Greater than one half but less than three quarters | 3 |
| Greater than three quarters up to whole area | 4 |
| Score equals A × B × 5 Total maximum = 80 | |
| Iris | |
| A. Values | |
| Folds above normal, congestion, swelling, circumcorneal injection (any one or all of these orcombination of any thereof), iris still reacting to light (sluggish reaction is positive) | 1 |
| No reaction to light, hemorrhage; gross destruction (any one or all of these) | 2 |
| Score equals A × 5 Total possible maximum = 10 | |
| Conjunctiva | |
| A. Redness (refers to palpebral conjunctiva only) | |
| Vessels definitely injected above normal | 1 |
| More diffuse, deeper crimson red, individual vessels not easily discernible | 2 |
| Diffuse beefy red | 3 |
| B. Chemosis | |
| Any swelling above normal (includes nictitating membrane) | 1 |
| Obvious swelling with partial eversion of the lids | 2 |
| Swelling with lids about half closed | 3 |
| Swelling with lids about half closed to completely closed | 4 |
| C. Discharge | |
| Any amount different from normal (does not include small amount observed in inner canthus of normal animals | 1 |
| Discharge with moistening of the lids and hairs just adjacent to the lids | 2 |
| Discharge with moistening of the lids and considerable area around the eye | 3 |

*(Draize J, Woodard G, Calvery H. 1944. Methods for the study of irritation and toxicity of substances applied topically to the skin and mucous membranes. J Pharm Exp Ther 82:377-390.)

[1] The maximum total score is the sum of all scores obtained for the cornea, iris and conjunctiva. Scores of 0 are assigned for each parameter if the cornea, iris, or conjunctiva is normal.

No toxicity or irritation was observed after single and 14-day-application. No difference between the treated and untreated eyes of all animals was detected. Very low score in the Draize test (practically zero) was established for both 5A and 5B tests.

Example 6. Efficacy of Particle Dispersion, Loaded with 0.1% Loratadine on Histamine Induced Wheals A. Evaluation of the Effect of Topical Application of SLNs Loaded with Loratadine on Histamine Induced Wheals.

Rabbits weighting 4.183±0.421 kg (males) and 4.661±0.542 kg (females) were used for the test. The day before the test a zone sized 10×7 cm was shaved on the back of each rabbit with electric razor. At the day of the test rabbits with skin defects were excluded.

Figure 22:
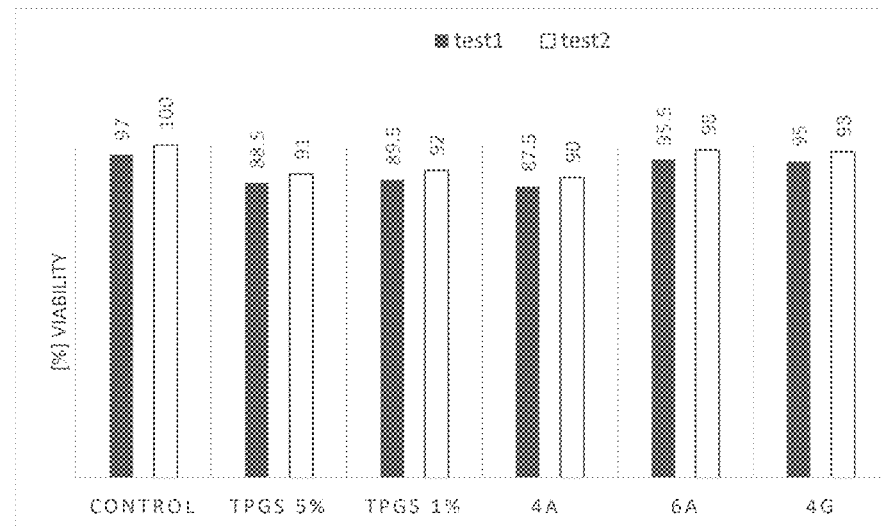
FIG. 22 shows a viability cell count (HaCaT) after 30 min incubation with different formulations: TPGS 5%; TPGS 1% (example 1A); compositions 1A; 3A and 1G.
Figure 23:
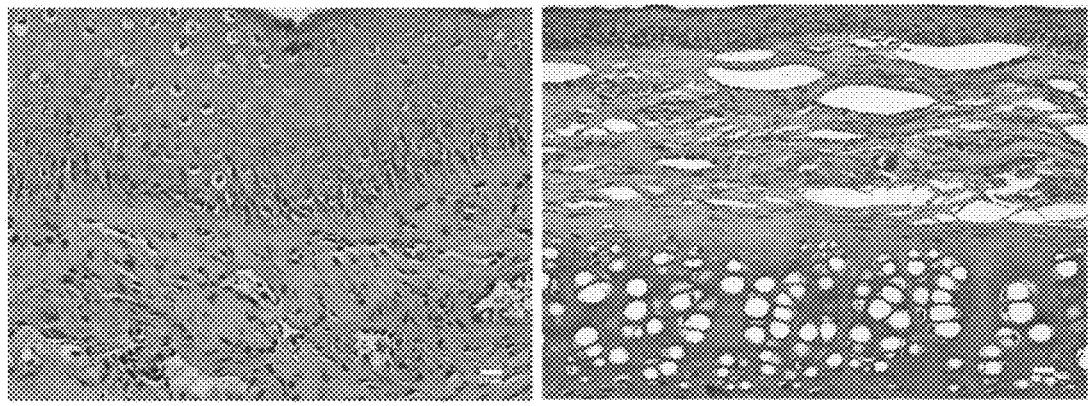
FIG. 23 shows light photomicrographs of cross-sections from biopsy samples of treatment groups A, B and C., FIGS. (21a), (21b), (21c) from the right (R) and left (L) nasal vestibules, demonstrating the presence of normal stratified squamous epithelium. Respectively 21a L×400; 21a R×260; 21b L×260; 21b R×360; 21c L×360 and 21c R×300; bar 1 cm; H&E.
Figure 23:
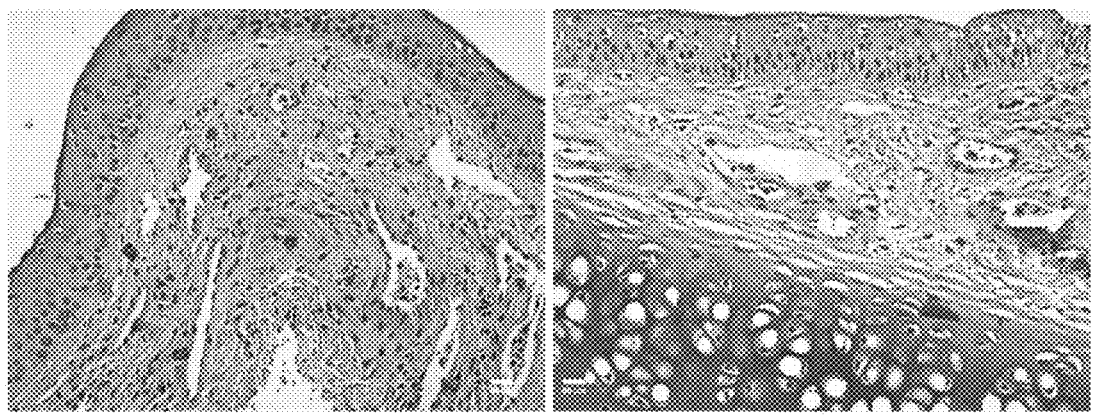
Figure 23:
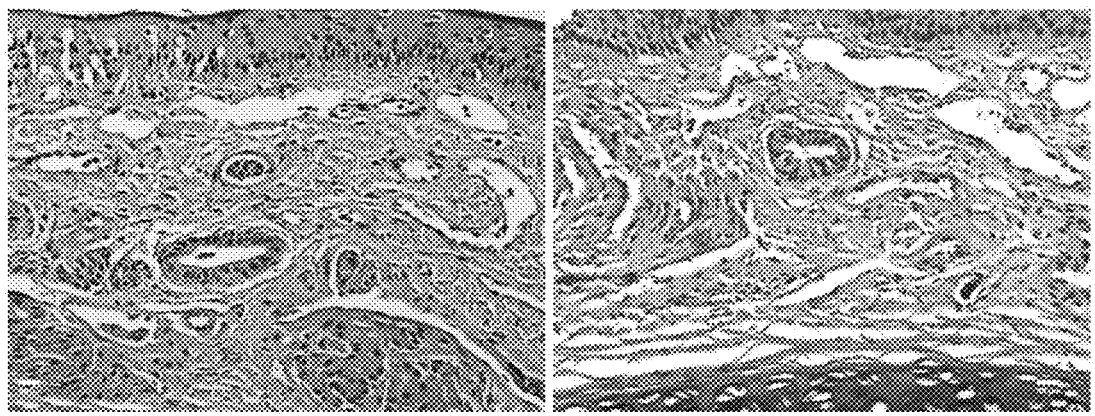

Six zones each sized 30×30 mm were sketched on the shaved area (FIG. 22).

Four males and two females were pretreated with the test formulations.

Zone HL was treated with 100 µl Fenistil gel, zone TL was treated with 100 µl 3A, zone TR was treated with 100 µl 3B and the other zones were left untreated. After 15 minutes the formulations were gently cleaned with cotton and water and intradermal injections of 40 µl histamine dihydrochloride solution (1 mg/ml) were applied to zones HL (Fenistil gel), HR (untreated control), TL (3A) and TR (3B). Zone MR was injected with 40 µl sodium chloride 0.9% and zone ML was only pricked.

Figure 25:
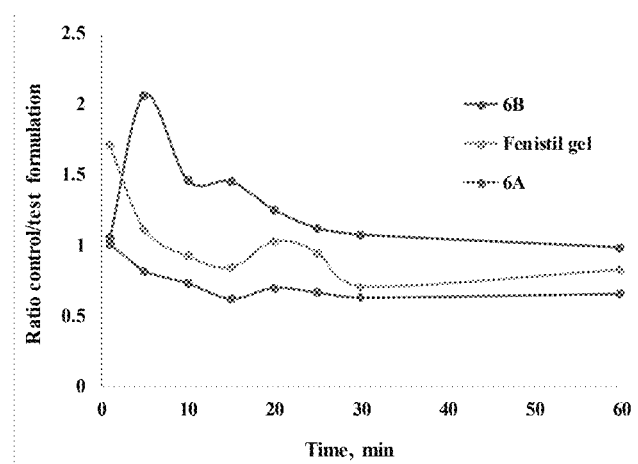
FIG. 25 shows evaluation of the effect of topical application of SLNs loaded with Loratadine, Fenistil gel and placebo SLNs on histamine induced wheals (mean, n=6).

The reaction towards histamine was photographed with digital camera at $1^{th}$, $5^{th}$, $10^{th}$, $15^{th}$, $20^{th}$, $25^{th}$, $30^{th}$ and $60^{th}$ minute post injections of histamine solution. The size of the wheals was determined on the obtained images with the use of ImageJ software. The results are presented as ratio between the size of the control from zone HR to the size of the wheal from tested zone (FIG. 25).

The test SLNs dispersion loaded with 0.1% Loratadine (3A) showed faster and stronger antihistamine effect compared to the marketed product Fenistil gel. Surprisingly, the placebo treated wheals were bigger in diameter compared to the control. Still, placebo treated wheals were sensibly softer and diffuse then the control treated ones which leads to the assumption that placebo SLNs alone contribute for faster resolution of the wheals. After the application of histamine injection, the size of wheals, pretreated with Fenistil gel, grew in a slower manner within the time before the $5^{th}$ min, compared to composition 3A. The probable reason can be finding in the full molecular availability compared to the "locked" Loratadine within the SLNs. However, after the $1^{st}$ min. the composition 3A expressed a sharp incline and on the $5^{th}$ min showed twice the effect of Fenistil gel.

B. Effect of Intradermal Injection of Placebo SLNs on Histamine Induced Wheals.

Studying the effect of topical application of placebo on the size and texture of the wheals, further co-administration experiment was conducted of placebo SLNs to the histamine intra dermal injection.

Rabbits weighting 4.183±0.421 kg (males) and 4.661±0.542 kg (females) were used for the test. The day before the test a zone sized 10×7 cm was shaved on the back of each rabbit with electric razor. At the day of the test rabbits with skin defects were excluded.

Figure 24:
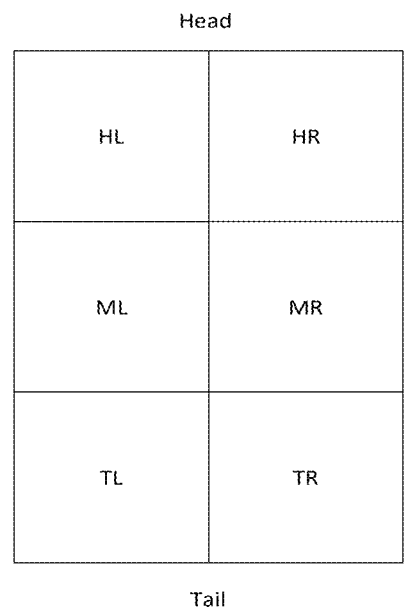
FIG. 24 shows a scheme of the wheal/treatment zones. HR—Head Right; HL—Head Left; MR—Middle Right; ML—Middle Left; TR—Tail Right; TL—Tail Left.

Six zones each sized 30×30 mm were sketched on the shaved area (FIG. 24).

Five males and one female were selected for the experiment. Zones HR and TR were treated with intra dermal injection of mixture 1:1 of histamine solution and sodium chloride. Zone HL was treated with mixture of 1:1 of histamine solution (2 mg/ml):3A.

Figure 26:
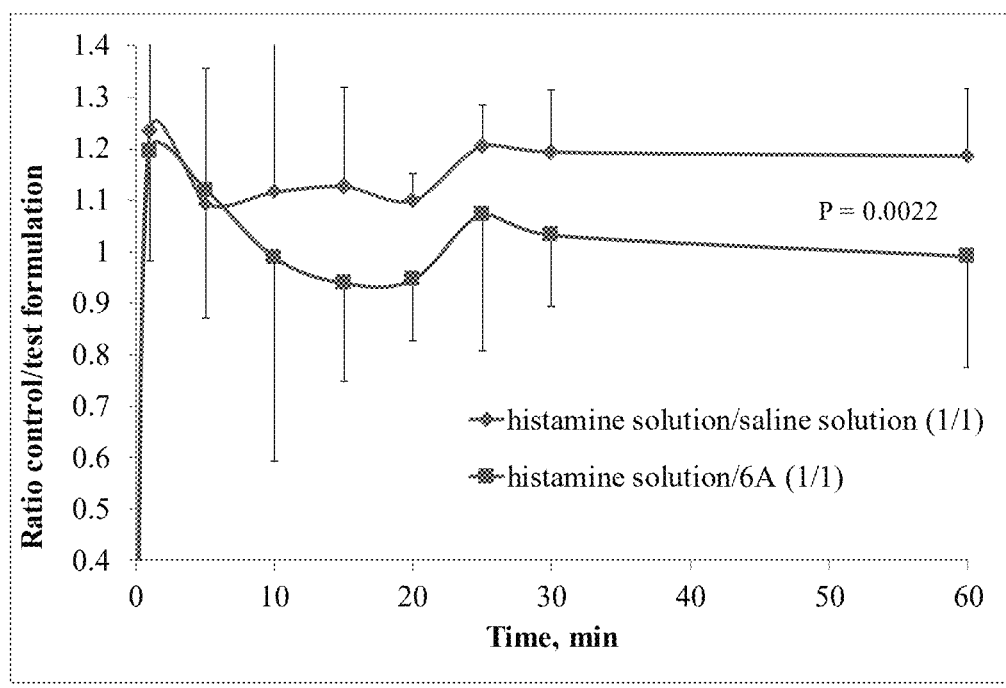
FIG. 26 shows evaluation of the effect of intradermal injection of placebo SLNs on histamine induced wheals (mean±SD, n=6)

The reaction towards histamine was photographed with digital camera at 5th, 10th, 15th, 20th, 25th, 30th and 60th minute post injections of histamine solution. The size of the wheals was determined on the obtained images with the use of Image J software. The results were presented as ratio between the sizes of the control from zone HR to the size of the wheal from tested zone (FIG. 26).

Surprisingly, the wheals were smaller in the group treated with histamine solution/3A. This comes to show that placebo SLNs doesn't increase and in fact decrease the effect of injected histamine, thus ensuring their safety use as carriers. It is likely that the combination of particle ingredients, namely, carnauba fatty acid esters and acids, tocotrienols and tocopherols possess notable anti-inflammatory effects.

The invention claimed is:

1. A method for targeted intracellular release of an active substance, said method comprising administering to a target tissue a solid lipid nanoparticle comprising a lipid, a surface acting agent, water and an active compound,
wherein:
said solid lipid nanoparticle is a solid lipid nanoparticle with spherical shape with a diameter of 15-100 nm;
said lipid is natural or synthetic carnauba wax mixed with a liquid lipid with 30% tocotrienol content relative to total amount of said liquid lipid, where the liquid lipid is in an amount up to 20 weight percentage of total amount of said lipid;
said surface acting agent is d-α-Tocopheryl polyethylene glycol 1000 succinate in combination with polysorbate;
said active compound is incorporated in said nanoparticles; and
components of said solid lipid nanoparticle are in the following quantitative ratios in w/w parts, relative to 100 parts, wherein 100 parts is total weight of said solid lipid nanoparticle: from 1-5 parts carnauba wax, from 0.2-1 parts liquid lipid, from 0.5 to 2.5 parts d-α-Tocopheryl polyethylene glycol 1000 succinate, from 0.7 to 3.5 parts polysorbate, from 0.00001 to 10 parts active substance, and water in the amount up to 100 parts, wherein the in-vitro release for 24 hours is between 2.2% and 4.1% and it occurs completely only after cellular internalization and subsequent in-place particle digestion.

2. A method for targeted intracellular release of an active substance according to claim 1, wherein the liquid lipid is selected from the group consisting of natural or synthetic red palm oil, rice bran oil, wheat germ oil or animal oils.

3. A method for targeted intracellular release of an active substance according to claim 2, wherein the liquid lipid comprises mono- or mix from isomers of Tocotrienol.

4. A method for targeted intracellular release of an active substance according to claim 1, wherein the polysorbate is selected from polysorbate 20, polysorbate 40, polysorbate 60 or polysorbate 80.

5. A method for targeted intracellular release of an active substance according to claim 4, wherein the polysorbate is polysorbate 40.

6. A method for targeted intracellular release of an active substance according to claim 1, wherein the active substance is drug substances, diagnostic agents, biological products, food supplements, or cosmetic products.

7. A method for intracellular release of an active substance according to claim 1, wherein said target tissue is a nasal mucosa.

8. A method for intracellular release of an active substance according to claim 1, wherein said liquid lipid comprises red palm oil with 30% tocotrienol, in an amount up to 20% of the total lipid.

9. A method for intracellular release of an active substance according to claim 1, wherein said lipid nanoparticle is a solid lipid nanoparticle with spherical shape with a diameter of 15-35 nm.

* * * * *